US007972607B2

(12) United States Patent
Tempel et al.

(10) Patent No.: US 7,972,607 B2
(45) Date of Patent: Jul. 5, 2011

(54) ATTENUATED FRANCISELLA AND METHODS OF USE

(75) Inventors: Rebecca Tempel, Portland, OR (US); Xin-He Lai, Portland, OR (US); Fred L. Heffron, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 298 days.

(21) Appl. No.: 12/280,272

(22) PCT Filed: Nov. 3, 2006

(86) PCT No.: PCT/US2006/043059
§ 371 (c)(1),
(2), (4) Date: Aug. 21, 2008

(87) PCT Pub. No.: WO2007/097789
PCT Pub. Date: Aug. 30, 2007

(65) Prior Publication Data
US 2010/0233211 A1    Sep. 16, 2010

Related U.S. Application Data

(60) Provisional application No. 60/776,701, filed on Feb. 23, 2006.

(51) Int. Cl.
*A61K 39/02* (2006.01)
*A61K 48/00* (2006.01)
*C12N 1/20* (2006.01)
*A01N 63/00* (2006.01)

(52) U.S. Cl. ............... 424/235.1; 424/234.1; 424/93.2; 435/252.3

(58) Field of Classification Search .................. None
See application file for complete search history.

(56) References Cited

U.S. PATENT DOCUMENTS
2010/0233211 A1* 9/2010 Tempel et al. ............ 424/234.1

FOREIGN PATENT DOCUMENTS
WO    WO 2004/084935 A2    10/2004
WO    WO 2005/049791 A2    6/2005

OTHER PUBLICATIONS

Deng et al, Infection and Immunity, Jul. 2006, 74/7:4224-4236.*
Qin et al, Infection and Immunity, Jul. 2008, 76/7:3086-3092.*
Isherwood et al, Advanced Drug Delivery Reviews, 2005, 57:1403-1414.*
Baker et al, Ann. N Y Acad., 2007, 1105:138-159.*
Larsson et al, Nature Genetics, Feb. 2005, 37/2:153-159.*
Tempel et al, Infection and Immunity, Sep. 2006, 74/9:5095-5105.*
Brotcke et al., "Identification of Mg1A-Regulated Genes Reveals Novel Virulence Factors in *Francisella tularensis*," *Infect. Immun.* 74:6642-6655, 2006.
Gray et al., "The Identification of Five Genetic Loci of *Francisella novicida* Associated with Intracellular Growth," *FEMS Microbiol. Lett.* 215:53-56, 2002.

Larsson et al., "The Complete Genome Sequence of *Francisella tularensis*, the Causative Agent of Tularemia," *Nature Genet.* 37:153-159, 2005.
Schulert et al., "*Francisella tularensis* Genes Required for Inhibition of the Neutrophil Respiratory Burst and Intramacrophage Growth Identified by Random Transposon Mutagenesis of Strain LVS," *Infect. Immun.* 77:1324-1336, 2009.
Weiss et al., "In Vivo Negative Selection Screen Identifies Genes Required for *Francisella* Virulence," *Proc. Natl. Acad. Sci. USA* 104:6037-6042, 2007.
Dennis et al., "Tularemia as a Biological Weapon," *JAMA* 285:2763-2773, 2001.
Ellis et al., "Tularemia," *Clin. Microbiol.Rev.* 15:631-646, 2002.
Golovliov et al., "A method for allelic replacement in *Francisella tularensis*," *FEMS Microbiol. Lett.* 222:273-280, 2003.
Havlasová et al., "Mapping of Immunoreactive Antigens of *Francisella tularensis* Live Vaccine Strain," *Proteomics* 2:857-867, 2002.
Kawula et al., "Use of Transposon-Transposase Complexes to Create Stable Insertion Mutant Strains of *Francisella tularensis* LVS," *Appl. Environ. Microbiol.* 70:6901-6904, 2004.
Krakauer, "Levels of Interleukin 6 and Tumor Necrosis Factor in Serum from Humans Vaccinated with Live, Attenuated *Francisella tularensis*," *Clin. Diagn. Lab. Immunol.* 2:487-488, 1995.
Nano et al., "A *Francisella tularensis* Pathogenicity Island Required for Intramacrophage Growth," *J. Bacteriol.* 186:6430-6436, 2004.
Oyston and Quarry, "Tularemia Vaccine: Past, Present and Future," *Antonie van Leeuwenhoek* 87:277-281, 2005.
Shen et al., "Mice Sublethally Infected with *Francisella novicida* U112 Develop Only Marginal Protective Immunity Against Systemic or Aerosol Challenge With Virulent Type A or B Strains of *F. tularensis*," *Microbial. Pathogenesis* 37:107-110, 2004.
Tempel et al., "*F. novicida* Transposon Mutants Attenuated for Growth in Macrophages and Mice," Oral presentation in Canada for the Pacific Northwest Meeting on Tularemia, Aug. 19, 2005.
Tempel et al., "*Francisella* Transposon Mutants Attenuated in Macrophages Protect Against Wild-Type Challenge in Mice," Oral presentation in Sweden, Nov. 25-30, 2005. Tempel et al., "*Francisella* Transposon Mutants Attenuated in Macrophages Protect Against Wild-Type Challenge in Mice," Poster presentation at Woods Hole, MA, Nov. 1-4, 2006.
Tempel et al., "*Francisella* Transposon Mutants Attenuated in Macrophages Protect Against Wild-Type Challenge in Mice," Poster presentation at Jiminy Peak Resort, MA, Nov. 6-8, 2005.
Tempel et al., "Attenuated *Francisella novicida* Transposon Mutants Protect Mice Against Wild-Type Challenge," *Infect. Immun.* 74:5095-5105, 2006.
Twine et al., "A Mutant of *Francisella tularensis* Strain SCHU S4 Lacking the Ability to Express a 58-Kilodalton Protein is Attenuated for Virulence and Is an Effective Live Vaccine," *Infect. Immun.* 73:8345-8352, 2005.
Wu et al., "Intranasal Vaccination Induces Protective Immunity against Intranasal Infection with Virulent *Francisella tularensis* Biovar A," *Infect. Immun.* 73:2644-2654, 2005.
Tularemia Workshop 2005 Program, Nov. 6-8, 2005, Jiminy Peak Mountain Resort, Hancock, MA.
Tularemia from Wikipedia, Dec. 9, 2005.

* cited by examiner

*Primary Examiner* — N M Minnifield
(74) *Attorney, Agent, or Firm* — Klarquist Sparkman, LLP

(57) ABSTRACT

*Francisella tularensis* is the bacterial pathogen that causes tularemia in humans and a number of animals. To date, no approved vaccine exists for this widespread and life-threatening disease. The present disclosure provides attenuated *Francisella* mutants that include functional deletions in one or more of the dsbB, FTT0742, pdpB, fumA, and carB genes. Also provided are immunogenic compositions that include the attenuated bacteria. Methods are provided for treatment using the attenuated *Francisella* mutants.

20 Claims, 6 Drawing Sheets

FIG. 6

SEQUENCE LISTING

```
<160> NUMBER OF SEQ ID NOS: 17

<210> SEQ ID NO 1
<211> LENGTH: 25
<212> TYPE: DNA
<213> ORGANISM: Artificial
<220> FEATURE:
<223> OTHER INFORMATION: primer

<400> SEQUENCE: 1
gttgaccagg cggaacatca atgtg                                         25

<210> SEQ ID NO 2
<211> LENGTH: 27
<212> TYPE: DNA
<213> ORGANISM: Artificial
<220> FEATURE:
<223> OTHER INFORMATION: primer to amplify dsbB from F. tularensis.

<400> SEQUENCE: 2
gggccctggc gccgttagag atatgtt                                       27

<210> SEQ ID NO 3
<211> LENGTH: 30
<212> TYPE: DNA
<213> ORGANISM: Artificial
<220> FEATURE:
<223> OTHER INFORMATION: primer to amplify dsbB from F. tularensis.

<400> SEQUENCE: 3
cccatgtgta aatcaatcac cggaacaatc                                    30

<210> SEQ ID NO 4
<211> LENGTH: 34
<212> TYPE: DNA
<213> ORGANISM: Artificial
<220> FEATURE:
<223> OTHER INFORMATION: primer to amplify dsbB from F. tularensis.

<400> SEQUENCE: 4
ggtgattgat ttacacatgg gacatggttt ccaa                               34

<210> SEQ ID NO 5
<211> LENGTH: 28
<212> TYPE: DNA
<213> ORGANISM: Artificial
<220> FEATURE:
<223> OTHER INFORMATION: primer to amplify dsbB from F. tularensis.

<400> SEQUENCE: 5
gtcgacattt gcatatgttg cttgaaca                                      28

<210> SEQ ID NO 6
<211> LENGTH: 30
<212> TYPE: DNA
<213> ORGANISM: Artificial
<220> FEATURE:
<223> OTHER INFORMATION: primer to amplify FTT0742 from F. tularensis.

<400> SEQUENCE: 6
```
ctcgagatgg tatagataca ccccagccag                                        30

<210> SEQ ID NO 7
<211> LENGTH: 43
<212> TYPE: DNA
<213> ORGANISM: Artificial
<220> FEATURE:
<223> OTHER INFORMATION: primer to amplify FTT0742 from F. tularensis.

<400> SEQUENCE: 7
attgctttag ttggctgcgg ttatattcca cacacggcga acg                         43

<210> SEQ ID NO 8
<211> LENGTH: 48
<212> TYPE: DNA
<213> ORGANISM: Artificial
<220> FEATURE:
<223> OTHER INFORMATION: primer to amplify FTT0742 from F. tularensis.

<400> SEQUENCE: 8
gttcgccgtg tgtggaatat aaccgcagcc aactaaagca ataggtag                    48

<210> SEQ ID NO 9
<211> LENGTH: 30
<212> TYPE: DNA
<213> ORGANISM: Artificial
<220> FEATURE:
<223> OTHER INFORMATION: primer to amplify FTT0742 from F. tularensis.

<400> SEQUENCE: 9
agatctaccc tgatctatcc aacgtgatgg                                        30

<210> SEQ ID NO 10
<211> LENGTH: 30
<212> TYPE: DNA
<213> ORGANISM: Artificial
<220> FEATURE:
<223> OTHER INFORMATION: primer to amplify pdpB from F. tularensis.

<400> SEQUENCE: 10
ctcgagagca ctttggacta agcacaaacc                                        30

<210> SEQ ID NO 11
<211> LENGTH: 45
<212> TYPE: DNA
<213> ORGANISM: Artificial
<220> FEATURE:
<223> OTHER INFORMATION: primer to amplify pdpB from F. tularensis.

<400> SEQUENCE: 11
caaagaccat aaaaaatgca tgtacctggg taatcaagca caaag                       45

<210> SEQ ID NO 12
<211> LENGTH: 46
<212> TYPE: DNA
<213> ORGANISM: Artificial
<220> FEATURE:
<223> OTHER INFORMATION: primer to amplify pdpB from F. tularensis.

<400> SEQUENCE: 12
tgcttgatta cccaggtaca tgcattttttt atggtctttg aggcag                     46

<210> SEQ ID NO 13
<211> LENGTH: 29
<212> TYPE: DNA
<213> ORGANISM: Artificial

```
<220> FEATURE:
<223> OTHER INFORMATION: primer to amplify pdpB from F. tularensis

<400> SEQUENCE: 13
agatctccaa ccattgttgc tgtagaacc                                         29

<210> SEQ ID NO 14
<211> LENGTH: 30
<212> TYPE: DNA
<213> ORGANISM: Artificial
<220> FEATURE:
<223> OTHER INFORMATION: primer to amplify fumA from F. tularensis.

<400> SEQUENCE: 14
ctcgaggctc accaattagt gaccatcctc                                        30

<210> SEQ ID NO 15
<211> LENGTH: 45
<212> TYPE: DNA
<213> ORGANISM: Artificial
<220> FEATURE:
<223> OTHER INFORMATION: primer to amplify fumA from F. tularensis.

<400> SEQUENCE: 15
aaagtttagg accttgctga tcacgctgat atgcttcata cattg                       45

<210> SEQ ID NO 16
<211> LENGTH: 46
<212> TYPE: DNA
<213> ORGANISM: Artificial
<220> FEATURE:
<223> OTHER INFORMATION: primer to amplify fumA from F. tularensis.

<400> SEQUENCE: 16
tatgaagcat atcagcgtga tcagcaaggt cctaaacttt ggaaac                      46

<210> SEQ ID NO 17
<211> LENGTH: 30
<212> TYPE: DNA
<213> ORGANISM: Artificial
<220> FEATURE:
<223> OTHER INFORMATION: primer to amplify fumA from F. tularensis.

<400> SEQUENCE: 17
agatctaatt agcgaggttg gcaagaggag                                        30
```

ATTENUATED FRANCISELLA AND METHODS OF USE

CROSS REFERENCE TO RELATED APPLICATIONS

This is the U.S. National Stage of International Application No. PCT/US2006/043059, filed Nov. 3, 2006 (published in English under PCT Article 21(2)), which claims the benefit of U.S. Provisional Application No. 60/776,701 filed Feb. 23, 2006, both of which are herein incorporated by reference.

ACKNOWLEDGMENT OF GOVERNMENT SUPPORT

This work was supported by National Institutes of Health R21 grant number EB000985, and National Science Foundation Graduate Research Fellowship No. GVPR5002A. Therefore, the Government of the United States of America may have certain rights in this application.

FIELD

This disclosure relates to attenuated *Francisella* bacteria and methods of their use, for example to stimulate an immune response in a mammal.

BACKGROUND

*Francisella tularensis* is a Gram-negative, facultative intracellular pathogen that causes tularemia, a debilitating and potentially fatal disease that affects humans and a wide range of animals. Infections can be acquired through bites from an arthropod vector, skin lesions, ingestion of contaminated food or water, and by inhalation of as few as 10 bacteria (Dennis et al., *JAMA* 285:2763-73, 2001). The low dose required to cause tularemia by aerosol route resulted in the development of *F. tularensis* for use as a biological weapon by several national weapons programs. The U.S. Centers for Disease Control and Prevention (CDC) classified *F. tularensis* as a Category A bioterrorism agent, members of which are considered most serious in posing a risk to national security. There is currently no approved vaccine available in the U.S. or Europe. Thus, the development of a vaccine against *F. tularensis* is an international priority.

Although the molecular mechanisms of *F. tularensis* pathogenesis remain obscure, replication in human and animal macrophages is central to the organism's ability to cause tularemia (Fortier et al., *Immunol. Ser.* 60:349-61, 1994). Several *F. tularensis* genes associated with intracellular growth have been identified, including iglB, iglC, mglA, pdpD, and a clpB homolog (Baron and Nano. *Mol. Microbiol.* 29:47-259, 1998; Golovliov et al., *FEMS Microbiol. Lett.* 222:273-80, 2003; Gray et al., *FEMS Microbiol. Lett.* 215:53-6, 2002; Lai et al., *Microb. Pathog.* 37:225-30, 2004; and Lauriano et al., *Proc. Natl. Acad. Sci. USA* 101:4246-9, 2004). Although many of the genes in the *F. tularensis* pathogenicity island (FPI) have been proposed to contribute to its survival and growth in macrophages (Larsson et al., *Nat. Genet.* 37:153-9, 2005; Nano et al., *J. Bacteriol.* 186:6430-6, 2004) none have arisen as potential vaccine candidates.

Four main subspecies of *F. tularensis* are commonly recognized: *tularensis* (type A), *holarctica* (type B), *novicida*, and *mediasiatica*. All of these biotypes share greater than 95% DNA sequence identity (Broekhuijsen et al., *J. Clin. Microbiol.* 41:2924-31, 2003). Although type A and type B strains are highly infectious, only type A strains cause significant mortality in humans. The current live vaccine strain (LVS) is an attenuated type B strain that provides varying levels of protection against challenge with type A *F. tularensis* strains (Chen, et al., *Microb. Patholg.* 36:311-8, 2004; Chen et al., *Vaccine* 21:3690-700, 2003; Conlan et al., *Vaccine* 23:2477-85, 2005; Green et al., *Vaccine* 23:2680-6, 2005; Shen, et al., *Vaccine* 22:2116-21, 2004; Wu et al., *Infect. Immun.* 73:2644-54, 2005). However, several limitations prevent the licensing of this vaccine. For example, the genetic basis of LVS attenuation and protection remains unknown. In addition, culturing LVS under certain conditions can lead to poorly immunogenic colony variants, demonstrating this organism's genetic instability (Cowley et al., *Mol. Microbiol.* 20:867-74, 1996; Eigelsbach and Downs. *J. Immunol.* 87:415-25, 1961). Also, this vaccine does not confer protection to all vaccinated subjects (McCrumb, *Bacteriol. Rev.* 25:262-7, 1961; Saslaw et al., *Arch. Intern. Med.* 107:702-14, 1961). Furthermore, LVS protection against aerosol challenge is variable and depends on the route of immunization as well as the host (Chen, et al., *Microb. Patholg.* 36:311-8, 2004; Chen et al., *Vaccine* 21:3690-700, 2003; Conlan et al., *Vaccine* 23:2477-85, 2005; and Shen et al., *Vaccine* 22:2116-21, 2004). This last point is relevant when considering *F. tularensis* as a biological weapon, as aerosol dispersal is the most likely route of delivery. These limitations demonstrate the need for an approved tularemia vaccine.

SUMMARY

While *F. novicida* is not generally considered a human pathogen, it displays a similar, if not greater, degree of virulence in mice as other *F. tularensis* subspecies. Moreover, *F. novicida* is much easier to manipulate genetically than *F. tularensis*. In addition to their considerable genomic similarity, the close relationship between *F. novicida* and *F. tularensis* is further highlighted by their nearly identical 16S rDNA sequences. This degree of genetic identity indicates that the two organisms utilize similar virulence genes, and that *F. novicida* is an apt platform for the development of attenuated *Francisella* bacteria that can be used in immunogenic compositions, such as a tularemia vaccine.

The categorization of *Francisella tularensis* as a Class A bioterrorism agent by the CDC demonstrates that this organism is acknowledged as a potential threat to national security. Thus, an immediate need exists for an effective immunogenic composition that can be used to treat (such as prevent) tularemia.

Using transposon mutagenesis, random insertions were made in an *F. novicida* genome, and the resulting mutant strains were analyzed for intracellular growth defects in macrophages, attenuation in mice, and the ability to confer protection against wild-type infection. The inventors identified 28 *F. novicida* transposon mutants that have a defect in intracellular growth in macrophage cell lines. Sixteen of these mutants exhibited 100% attenuation in mice at greater than 100-fold the wild-type $LD_{50}$. Upon challenge with the wild-type organism, five transposon mutant strains protected mice against infection with >8×10$^5$ cfu of wild-type *F. novicida*. The disrupted genes correspond to dsbB, FTT0742, pdpB, fumA, and carB in the *F. tularensis* strain SchuS4. These results indicate that functionally deleting one or more of these genes in other *F. tularensis* subspecies can be used to generate immunogenic compositions for use against pathogenic subspecies.

Provided herein are isolated *Francisella* bacterium, which are attenuated by functionally deleting or inactivating one or more of the following genes: dsbB, FTT0742, pdpB, fumA, and carB. One skilled in the art will appreciate that any species or variety of *Francisella* can be used, such as *Francisella tularensis*, for example *Francisella tularensis* subspecies *tularensis* or *Francisella tularensis* subspecies *novicida*. Methods of generating attenuated *Francisella* bacterium with the desired genes functionally deleted (or otherwise inactivated) are known in the art, and can include complete or partial deletion mutation or insertional mutation.

These functional deletions attenuate the bacterium, and reduce the risk of the bacterium reverting to a virulent from. Ideally, such functional deletions retain the ability of the isolated *Francisella* bacterium to stimulate a sufficient immune response in a mammal (such as a rodent or human) to provide the desired protection or treatment. For example, an effective amount of the disclosed attenuated *Francisella* bacteria can produce an immune response in a subject, and in some examples can treat a subject (such as a subject exposed to *Francisella* or who may become exposed to *Francisella* in the future).

In particular examples, the isolated *Francisella* bacterium disclosed herein include functional deletions in at least two of the following genes: dsbB, FTT0742, pdpB, fumA, and carB. For example, the isolated *Francisella* bacterium can include a functional deletion of the dsbB, FTT0742, and pdpB genes, or any two of these genes, such as dsbB and FTT0742, dsbB and pdpB, or FTT0742 and pdpB.

Also provided by the present disclosure are immunogenic compositions that include the disclosed isolated *Francisella* bacteria. In particular examples, such compositions can further include other biologically active or inactive agents, for example an adjuvant, a pharmaceutically acceptable carrier, or combinations thereof.

Methods are disclosed for eliciting an immune response against *Francisella* in a subject. In particular examples, the methods include administering a therapeutically effective amount of the disclosed attenuated *Francisella* bacteria (for example in an immunogenic composition), thereby eliciting an immune response against *Francisella* in the subject. Methods of administration are routine and known to those skilled in the art. In some examples, the subject is a mammal, such as a human or veterinary subject (such as a laboratory animal, dog, cat, sheep, or cow). In particular examples, the resulting immune response provides a prophylactic effect, for example in a subject who may be exposed to *Francisella* at a later date. In some examples, the resulting immune response treats tularemia in a subject, for example in a subject who was previously infected with or exposed to *Francisella*.

The foregoing and other objects and features of the disclosure will become more apparent from the following detailed description, which proceeds with reference to the accompanying figures.

BRIEF DESCRIPTION OF THE DRAWINGS

FIG. 6 is a schematic drawing outlining a method that can be used to functionally delete dsbB, FTT0742, pdpB, fumA, carB (or combinations thereof) in *F. tularensis*, for example to attenuate the bacteria.

SEQUENCE LISTING

Figure 1:
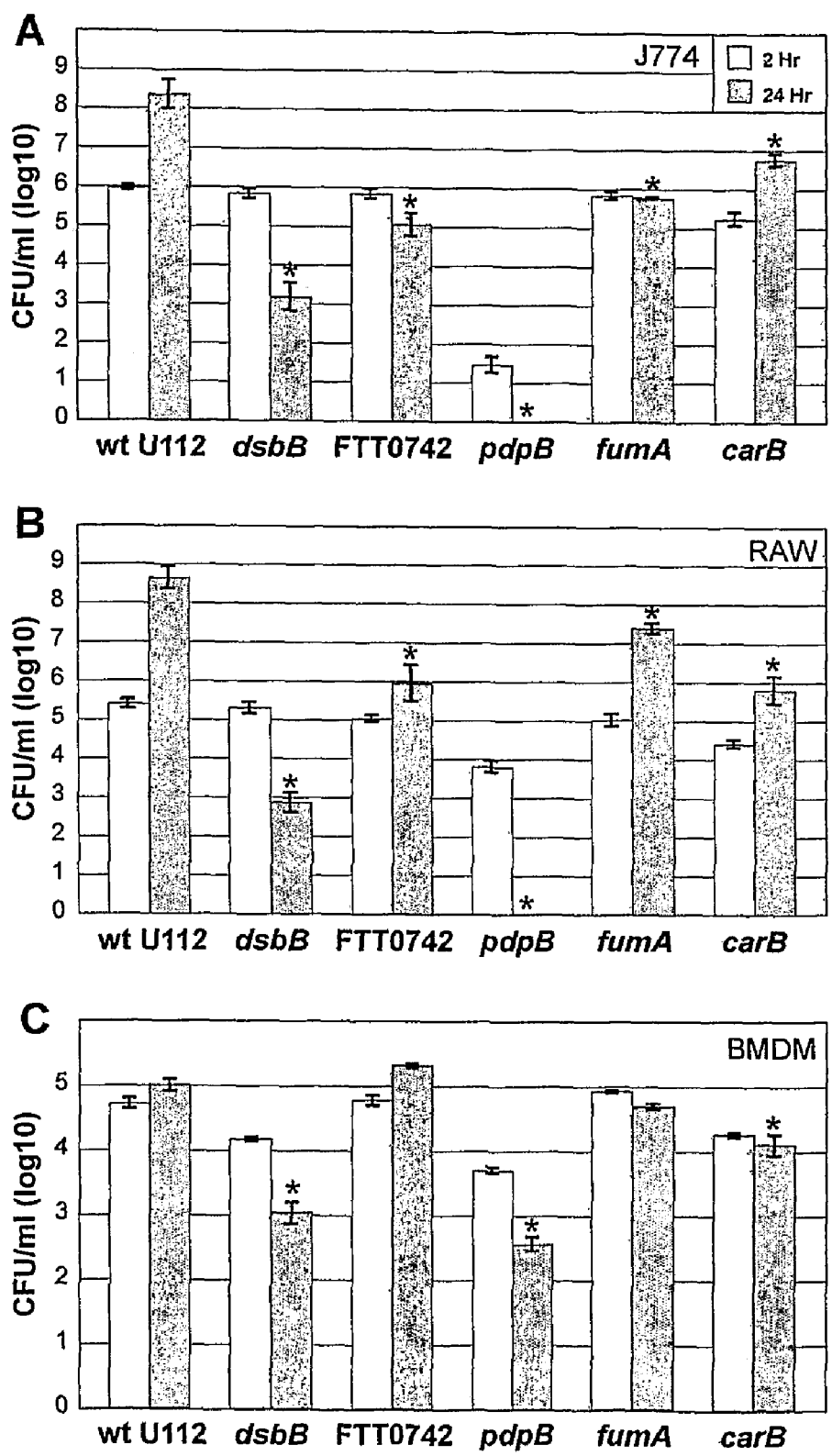
FIGS. 1A-C are bar graphs showing that the five *F. novicida* tranposon mutants are attenuated for growth in (A) J744, (B) RAW, and (C) THP-1 macrophages. Each column represents the average of three individual infections. No colonies were recorded for the pdpB mutants.
Figure 2:
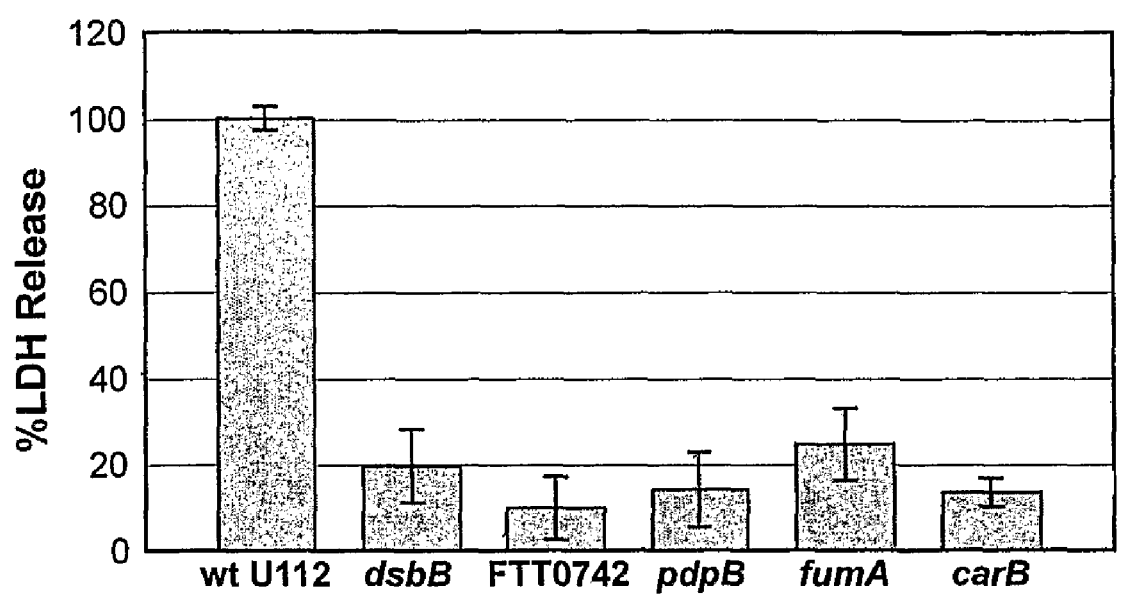
FIG. 2 is a bar graph showing that infection with the *F. novicida* mutants (dsbB, FTT0742, pdpB, fumA, carB) does not reduce host cell integrity, as indicated by the level of LDH release. Each column represents the average of three individual infections.
Figure 3:
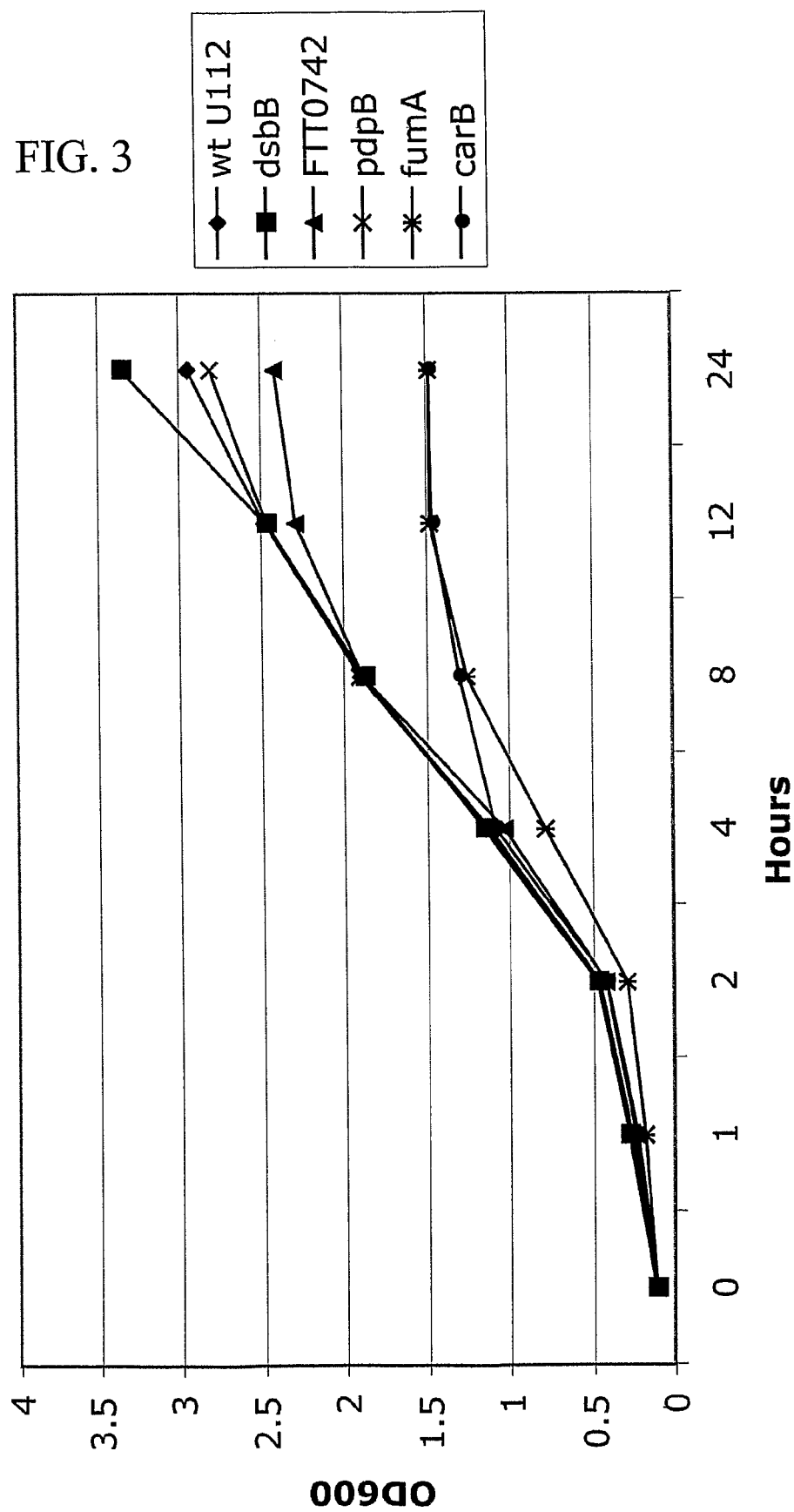
FIG. 3 is a graph showing that the *F. novicida* mutants (dsbB, FTT0742, pdpB, fumA, carB) do not exhibit major in vitro growth defects, as indicated by the optical density of cultures.
Figure 4:
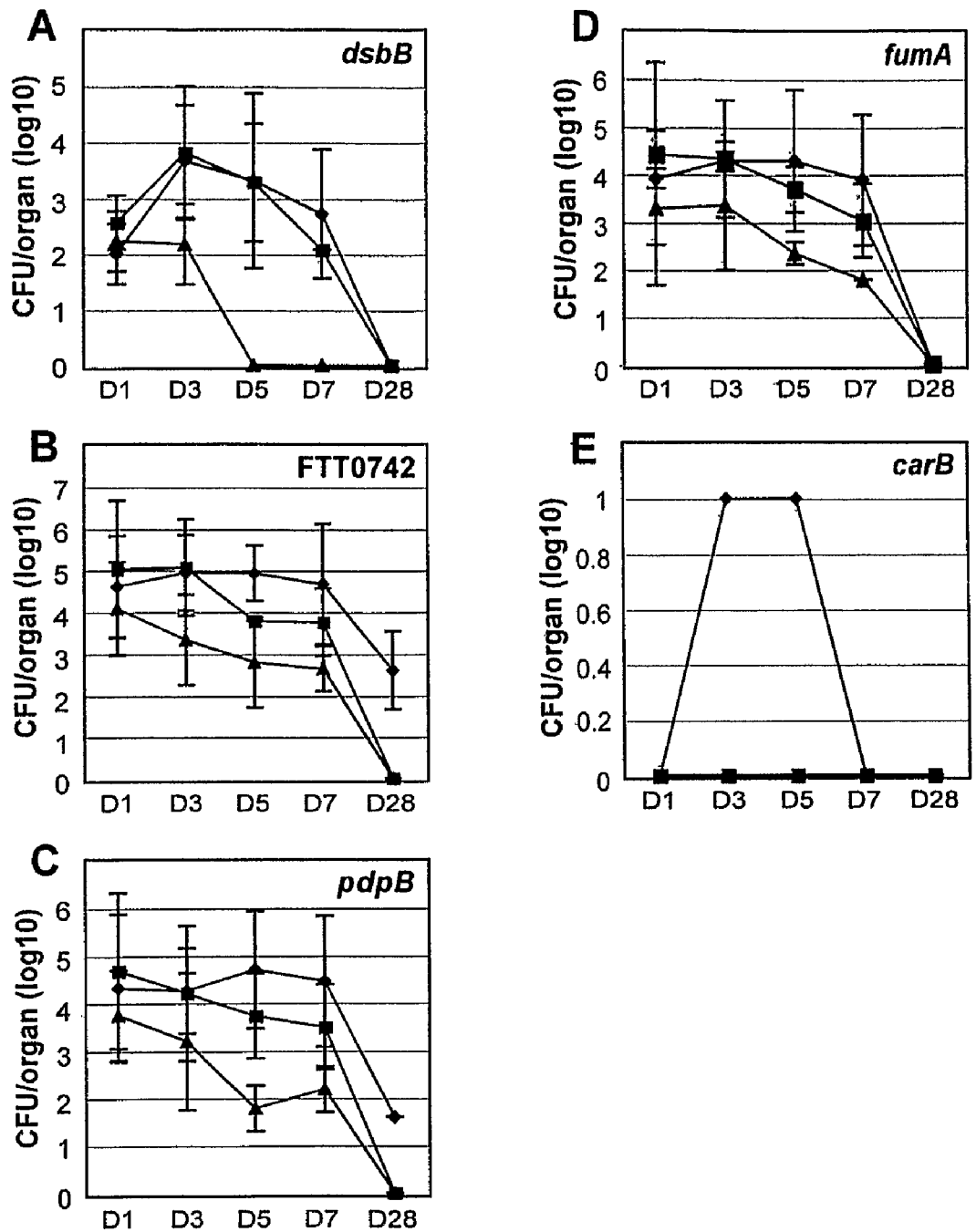
FIGS. 4A-4E are graphs showing that *F. novicida* mutants (A) dsbB, (B) FTT0742, (C) pdpB, (D) fumA, and (E) carB disseminate and are subsequently cleared from the (♦) spleen, (■) liver, and (▲) lungs.

SEQ ID NO: 1 is a primer sequence used to obtain the sequence of the fusion junction in *F. novicida* transposon mutants.

SEQ ID NOS: 2-5 are exemplary primer sequences that can be used to amplify the *F. tularensis* subsp. *tularensis* dsbB gene.

SEQ ID NOS: 6-9 are exemplary primer sequences that can be used to amplify the *F. tularensis* subsp. *tularensis* FTT0742 gene.

SEQ ID NOS: 10-13 are exemplary primer sequences that can be used to amplify the *F. tularensis* subsp. *tularensis* pdpB gene.

SEQ ID NOS: 14-17 are exemplary primer sequences that can be used to amplify the *F. tularensis* subsp. *tularensis* fumA gene.

DETAILED DESCRIPTION

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a pharmaceutically acceptable carrier" includes single or plural pharmaceutically acceptable carriers and is considered equivalent to the phrase "comprising at least one pharmaceutically acceptable carrier." The term "or" refers to a single element of stated alternative elements or a combination of two or more elements, unless the context clearly indicates otherwise. As used herein, "comprises" means "includes." Thus, "further comprising an adjuvant or a pharmaceutically acceptable carrier" means "including one or more adjuvants, including one or more pharmaceutically acceptable carriers, or including one or more adjuvants and one or more pharmaceutically acceptable carriers," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

CFU colony forming units

FPI *F. tularensis* pathogenicity island

LD$_{50}$ 50% lethal dose

Adjuvant: A compound, composition, or substance that when used in combination with an immunogenic agent (such as the attenuated *Francisella* bacteria disclosed herein) augments or otherwise alters or modifies a resultant immune response. In some examples, an adjuvant increases the titer of antibodies induced in a subject by the immunogenic agent. In another example, if the antigenic agent is a multivalent antigenic agent, an adjuvant alters the particular epitopic sequences that are specifically bound by antibodies induced in a subject.

Exemplary adjuvants include, but are not limited to, Freund's Incomplete Adjuvant (IFA), Freund's complete adjuvant, B30-MDP, LA-15-PH, montanide, saponin, aluminum salts such as aluminum hydroxide (Amphogel, Wyeth Laboratories, Madison, N.J.), alum, lipids, keyhole lympet protein, hemocyanin, the MF59 microemulsion, a mycobacterial antigen, vitamin E, non-ionic block polymers, muramyl dipeptides, polyanions, amphipatic substances, ISCOMs (immune stimulating complexes, such as those disclosed in European Patent EP 109942), vegetable oil, Carbopol, aluminium oxide, oil-emulsions (such as Bayol F or Marcol 52), *E. coli* heat-labile toxin (LT), Cholera toxin (CT), and combinations thereof.

In one example, an adjuvant includes a DNA motif that stimulates immune activation, for example the innate immune response or the adaptive immune response by T-cells, B-cells, monocytes, dendritic cells, and natural killer cells. Specific, non-limiting examples of a DNA motif that stimulates immune activation include CG oligodeoxynucleotides, as described in U.S. Pat. Nos. 6,194,388; 6,207,646; 6,214,806; 6,218,371; 6,239,116; 6,339,068; 6,406,705; and 6,429,199, and IL-2 or other immunomodulators.

Administration: To provide or give a subject an agent, such as an immunogenic composition disclosed herein, by any effective route. Exemplary routes of administration include, but are not limited to, oral, injection (such as subcutaneous, intramuscular, intradermal, intraperitoneal, and intravenous), sublingual, rectal, transdermal, intranasal, intraocular, and inhalation routes.

Antibody: A molecule including an antigen binding site which specifically binds (immunoreacts with) an antigen. Examples include polyclonal antibodies, monoclonal antibodies, humanized monoclonal antibodies, or immunologically effective portions thereof. In a particular example, a subject produces antibodies when exposed to attenuated *Francisella* bacteria of the present application.

Immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Antigen: A compound, composition, or substance that can stimulate the production of antibodies or a T-cell response in an animal, including compositions that are administered to an animal. An antigen reacts with the products of specific humoral or cellular immunity, including those induced by heterologous immunogens. The term "antigen" includes all related antigenic epitopes. In one example, an antigen is an attenuated *Francisella* bacterium that includes one or more functionally deleted dsbB, FTT0742, pdpB, fumA, or carB genes (or combinations thereof).

Attenuated bacterium: A bacterium having a decreased or weakened ability to produce disease (for example having reduced virulence) while retaining the ability to stimulate an immune response like that of the natural (or wild-type) bacterium. In one example, a live bacterium is attenuated by functionally deleting one or more genes of the bacterium, such as functionally deleting at least two genes. In a particular example, live *Francisella* is attenuated by functionally deleting at one or more of (such as two, three, four or five of) dsbB, FTT0742, pdpB, fumA, or carB (or combinations thereof).

Attenuated vaccine: An immunogenic composition that includes live pathogens (such as live *F. tularensis* subsp. *tularensis* having a functionally deleted dsbB, FTT0742, pdpB, fumA, or carB gene, or combinations thereof) that have decreased virulence but are still capable of inducing a protective immune response to the virulent forms of the pathogen.

Carbamoyl phosphate synthase (carB): The large subunit of heterodimeric enzyme carbamoyl phosphate synthase, which is involved in pyrimidine biosynthesis (Koonin and Galperin. 2003. Sequence—evolution—function: computational approaches in comparative genomics. Kluwer Academic, Boston). The term carB includes any carB gene, cDNA, mRNA, or protein, from *Francisella* that is a carB involved in pyrimidine biosynthesis. It is shown herein that functional deletion of the carB gene in *Francisella tularensis* subsp. *novicida* results in a bacterium that is able to infect macrophages and protect mammals (such as mice) against challenges with the wild-type bacterium.

*Francisella* carB sequences are publicly available. For example, GenBank Accession Nos: NC_006570 and YP_170571 disclose *Francisella tularensis* subsp. *tularensis* SCHU S4 carB nucleic acid and protein sequences, respectively. However, one skilled in the art will appreciate that a carB sequence can include allelic variants, variants, fragments, homologs or fusion sequences that retain carbamoyl phosphate synthase activity.

Cellular immunity: An immune response mediated by cells or the products they produce, such as cytokines, rather than by an antibody. Includes, but is not limited to, delayed type hypersensitivity and cytotoxic T cells.

DNA (deoxyribonucleic acid): A long chain polymer which includes the genetic material of most living organisms (many viruses have genomes containing only ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Disulfide bond formation protein B (dsbB): An integral membrane protein that is part of a pathway that leads to disulfide bond formation between cysteines in periplasmic proteins in *E. coli* and other bacteria (Kadokura et al., *Annu. Rev. Biochem.* 72:111-135, 2003). The term dsbB includes any dsbB gene, cDNA, mRNA, or protein, from *Francisella* that is a dsbB involved in pyrimidine biosynthesis. It is shown herein that functional deletion of the dsbB gene in *Francisella tularensis* subsp. *novicida* results in a bacterium that is able to infect macrophages and protect mammals (such as mice) against challenges with the wild-type bacterium.

*Francisella* dsbB sequences are publicly available. For example, GenBank Accession Nos: NC_006570 and YP_169177 disclose *Francisella tularensis* subsp. *tularensis* SCHU S4 dsbB nucleic acid and protein sequences, respectively. However, one skilled in the art will appreciate that a dsbB sequence can include allelic variants, variants, fragments, homologs or fusion sequences that retain the ability to promote disulfide bond formation between cysteines.

Epitope: Chemical groups or peptide sequences that are antigenic, that is, that elicit a specific immune response. An antibody binds a particular antigenic epitope, or a T-cell reacts with a particular antigenic epitope bound to a specific MHC molecule. In some examples, an epitope has a minimum sequence of 6-8 amino acids, and a maximum sequence of about 100 amino acids, for example, about 50, 25, or 18 amino acids in length.

*Francisella tularensis*: A Gram-negative bacterium that is the causative agent of tularemia. Subspecies of *F. tularensis* include *tularensis* (type A), *holarctica* (type B), *novicida*, and *mediasiatica*.

Fumarate hydratase A (fumA): The enzyme of the Kreb's cycle (citric acid cycle/CAC) that converts fumarate to malate (Tseng et al., *J. Bacteriol.* 183:461-7, 2001). The term fumA includes any fumA gene, cDNA, mRNA, or protein from *Francisella* that is a fumA that can convert fumarate to malate. It is shown herein that functional deletion of the fumA gene in *Francisella tularensis* subsp. *novicida* results in a bacterium that has lower levels of in vitro replication and can protect mammals (such as mice) against challenges with the wild-type bacterium.

*Francisella* fumA sequences are publicly available. For example, GenBank Accession Nos: NC_006570 and YP_170516 disclose *Francisella tularensis* subsp. *tularensis* SCHU S4 fumA nucleic acid and protein sequences, respectively. However, one skilled in the art will appreciate that a fumA sequence can include allelic variants, variants, fragments, homologs or fusion sequences that retain the ability to convert fumarate to malate.

Functional deletion: A mutation, such as a substitution, partial or complete deletion, insertion, or other variation, made to a gene sequence that significantly reduces (and in some cases eliminates) production of the gene product or renders the gene product substantially or completely non-functional. For example, a functional deletion of a dsbB, FTT0742, pdpB, fumA, or carB gene (or combinations thereof) in *F. tularensis* results in *F. tularensis* having substantially non-functional or non-existent dsbB, FTT0742, pdpB, fumA, or carB protein, which results in attenuation of the *F. tularensis* pathogen.

Humoral immunity: Immunity that can be transferred with immune serum from one subject to another. Typically, humoral immunity refers to immunity resulting from the introduction of specific antibodies or stimulation of the production of specific antibodies, for example by administration of an attenuated *F. tularensis* disclosed herein.

Immune response: A response of a cell of the immune system, such as a B-cell, T-cell, macrophage, monocyte, or polymorphonucleocyte, to an immunogenic agent (such as the disclosed attenuated *F. tularensis*) in a subject. An immune response can include any cell of the body involved in a host defense response, such as an epithelial cell that secretes interferon or a cytokine. An immune response includes, but is not limited to, an innate immune response or inflammation.

The response can be specific for a particular antigen (an "antigen-specific response"). In a particular example, an immune response is a T cell response, such as a CD4+ response or a CD8+ response. In another example, the response is a B cell response, and results in the production of specific antibodies to the immunogenic agent.

In some examples, such an immune response provides protection for the subject from the immunogenic agent or the source of the immunogenic agent. For example, the response can protect a subject, such as a human or veterinary subject, from infection by a pathogen (such as *F. tularensis*), or interfere with the progression of an infection by a pathogen. An immune response can be active and involve stimulation of the subject's immune system, or be a response that results from passively acquired immunity.

Immunity: The state of being able to mount a protective response upon exposure to an immunogenic agent (such as the disclosed attenuated *F. tularensis*). Protective responses can be antibody-mediated or immune cell-mediated, and can be directed toward a particular pathogen (such as *F. tularensis*). Immunity can be acquired actively (such as by exposure to an immunogenic agent, either naturally or in a pharmaceutical composition) or passively (such as by administration of antibodies).

Immunogen: An agent (such as a compound, composition, or substance) that can stimulate or elicit an immune response by a subject's immune system, such as stimulating the production of antibodies or a T-cell response in a subject. Immunogenic agents include, but are not limited to, pathogens (such as the disclosed attenuated *F. tularensis*) and their corresponding proteins. One specific example of an immunogenic composition is a vaccine.

Immunogenicity: The ability of an agent to induce a humoral or cellular immune response. Immunogenicity can be measured, for example, by the ability to bind to an appropriate MHC molecule (such as an MHC Class I or II molecule) and to induce a T-cell response or to induce a B-cell or antibody response, for example, a measurable cytotoxic T-cell response or a serum antibody response to a given epitope. Immunogenicity assays are well-known in the art and are described, for example, in Paul, Fundamental Immunology, 3rd ed., 243-247 (Raven Press, 1993) and references cited therein.

Immunologically Effective Dose: A therapeutically effective amount of an immunogen (such as the disclosed attenuated *F. tularensis*) that will treat (such as prevent), lessen, or attenuate the severity, extent or duration of a disease or condition, for example, infection by a pathogen or development of a disease resulting from infection (such as tularemia).

Isolated: To be significantly separated from other agents. An "isolated" biological component (such as a nucleic acid molecule or protein) has been substantially separated, produced apart from, or purified away from other biological components in the cell of the organism in which the component occurs, for example, other chromosomal and extra-chromosomal DNA and RNA, and proteins. Nucleic acid molecules and proteins which have been "isolated" include nucleic acid molecules and proteins purified by standard purification methods. The term also embraces nucleic acid molecules and proteins prepared by recombinant expression in a host cell as well as chemically synthesized proteins and nucleic acids. Samples of isolated biological components include samples of the biological component wherein the biological component represents greater than 90% (for example, greater than 95%, such as greater than 98%) of the sample.

An "isolated" microorganism (such as an attenuated *Francisella* bacterium) has been substantially separated or purified away from microorganisms of different types, strains, or species. Microorganisms can be isolated by a variety of techniques, including serial dilution and culturing.

Lymphocytes: A type of white blood cell involved in the immune defenses of the body. There are two main types of lymphocytes: B-cells and T-cells.

Mutation: A change in a nucleic acid sequence (such as a gene sequence) or amino acid sequence, for example as compared to a nucleic acid or amino acid sequence present in a wild-type or native organism. In particular examples, a mutation in one or more genes can attenuate a pathogen, such as a *F. tularensis*. Mutations can occur spontaneously, or can be introduced, for example using molecular biology methods. In particular examples, a mutation includes one or more nucleotide substitutions, deletions, insertions, or combinations thereof. In particular examples, the presence of one or more mutations in a gene can functionally delete (for example significantly inactivate) that gene.

Nucleic acid molecule: A deoxyribonucleotide or ribonucleotide polymer including, without limitation, cDNA, mRNA, genomic DNA, genomic RNA, and synthetic (such as chemically synthesized) DNA. Includes nucleic acid sequences that have naturally-occurring, modified, or non-naturally-occurring nucleotides linked together by naturally-occurring or non-naturally-occurring nucleotide linkages. Nucleic acid molecules can be modified chemically or biochemically and can contain non-natural or derivatized nucleotide bases. Such modifications include, for example, labels, methylation, substitution of one or more of the naturally occurring nucleotides with analogs, and internucleotide linkage modifications.

Nucleic acid molecules can be in any topological conformation, including single-stranded, double-stranded, partially duplexed, triplexed, hairpinned, circular, linear, and padlocked conformations. Where single-stranded, a nucleic acid molecule can be the sense strand or the antisense strand. Also included are synthetic molecules that mimic polynucleotides in their ability to bind to a designated sequence via hydrogen bonding and other chemical interactions. Such molecules are known and include, for example, molecules in which peptide linkages are substituted for phosphate linkages in the backbone.

Nucleotide: A subunit of DNA or RNA including a nitrogenous base (adenine, guanine, thymine, or cytosine in DNA; adenine, guanine, uracil, or cytosine in RNA), a phosphate molecule, and a sugar molecule (deoxyribose in DNA and ribose in RNA).

ORF FTT0742: A hypothetical lipoprotein that is predicted to have transmembrane regions, and thus may be a component of the *F. novicida* cell wall or involved in molecule transport. The term FTT0742 includes any FTT0742 gene, cDNA, mRNA, or protein, from *Francisella* that is a FTT0742 lipoprotein. It is shown herein that functional deletion of the FTT0742 gene in *Francisella tularensis* subsp. *novicida* results in a bacterium that has lower levels of in vitro replication and can protect mammals (such as mice) against challenges with the wild-type bacterium.

*Francisella* FTT0742 sequences are publicly available. For example, GenBank Accession Nos: NC_006570 and YP_169753 disclose *Francisella tularensis* subsp. *tularensis* SCHU S4 FTT0742 nucleic acid and protein sequences, respectively. However, one skilled in the art will appreciate that a FTT0742 sequence can include allelic variants, variants, fragments, homologs or fusion sequences that retain the ability to function as lipoproteins.

Passive immunity: Immunity acquired by the introduction by immune system components into a subject rather than by stimulation.

pdpB: An uncharacterized protein encoded on the *F. tularensis* pathogenicity island (FPI) that exhibits some similarity to the conserved bacterial protein IcmF. It has been shown that icmF is required for *Legionella pneumophila* intracellular growth, so pdpB may play a similar role in *F. novicida* intracellular growth. The pdpB sequence also has some homology to *Plasmodium rhoptry* proteins, which are involved in host cell binding and invasion. This, coupled with the reduced ability of pdpB mutants to enter host cells, suggests that the gene product of pdpB may also play a role in host cell invasion. The term pdpB includes any pdpB gene, cDNA, mRNA, or protein, from *Francisella* that functions as pdpB. It is shown herein that functional deletion of the pdpB gene in *Francisella tularensis* subsp. *novicida* results in a bacterium that has lower levels of in vitro replication and can protect mammals (such as mice) against challenges with the wild-type bacterium.

*Francisella* pdpB sequences are publicly available. For example, GenBank Accession No: NC_006570 disclose *Francisella tularensis* subsp. *tularensis* SCHU S4 pdpB nucleic acid and protein sequences (regions 1382427 . . . 1385708 and 1775771 . . . 1779052) and GenBank Accession Nos: AY293579 and AAP58967 disclose *Francisella tularensis* subsp. *novicida* pdpB nucleic acid and protein sequences, respectively. However, one skilled in the art will, appreciate that a pdpB sequence can include allelic variants, variants, fragments, homologs or fusion sequences.

Protein: Polymers of amino acids (typically L-amino acids) or amino acid mimetics linked through peptide bonds or peptide bond mimetic to form a chain. The terminal amino acid at one end of the chain typically has a free amino group (the amino-terminus), while the terminal amino acid at the other end of the chain typically has a free carboxyl group (the carboxy terminus). Encompasses any amino acid sequence and includes modified sequences such as glycoproteins. The terms cover naturally occurring proteins, as well as those which are recombinantly or synthetically produced.

Non-natural combinations of naturally- or non-naturally occurring sequences of amino acids may also be referred to as "fusion proteins."

Pharmaceutically Acceptable Carrier: Compositions or formulations suitable for pharmaceutical delivery of one or more therapeutic molecules, such as one or more immunogenic compositions that includes attenuated *Francisella* bacteria of the present disclosure. The pharmaceutically acceptable carriers (vehicles) useful in this disclosure are conventional (for example see Remington's Pharmaceutical Sciences, by E. W. Martin, Mack Publishing Co., Easton, Pa., 15th Edition (1975)).

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

Purified: The term purified does not require absolute purity; rather, it is intended as a relative term. Thus, for example, a purified attenuated *Francisella* bacterial preparation is one in which the bacteria are more enriched than the bacteria is in its natural environment (for example within a cell). In one example, a preparation is purified such that the purified bacteria represent at least 50% of the total content of the preparation. In other examples, a bacteria is purified to represent at least 90%, such as at least 95%, or even at least 98%, of all macromolecular species present in a purified preparation prior to admixture with other formulation ingredients, such as a pharmaceutical carrier, adjuvant or other co-ingredient. In some examples, the purified preparation is be essentially homogeneous, wherein other macromolecular species are not detectable by conventional techniques.

Such purified preparations can include materials in covalent association with the active agent, such as glycoside residues or materials admixed or conjugated with the active agent, which may be desired to yield a modified derivative or analog of the active agent or produce a combinatorial therapeutic formulation, conjugate, fusion protein or the like.

Quantitating: Determining a relative or absolute quantity of a particular component in a sample. For example, in the context of quantitating antibodies in a sample of a subject's blood to detect an immune response to a pathogen (such as the attenuated *Francisella* disclosed herein), quantitating refers to determining the quantity of antibodies using an antibody assay, for example, an ELISA-assay or a T-cell proliferation assay.

Recombinant: A recombinant nucleic acid molecule or protein is one that has a sequence that is not naturally occurring or has a sequence that is made by an artificial combination of two otherwise separated segments of sequence. In particular examples, this artificial combination is accomplished by chemical synthesis or by the artificial manipulation of isolated segments of nucleic acids, for example, by genetic engineering techniques such as those described in Sambrook et al. (ed.), Molecular Cloning: A Laboratory Manual, 2nd ed., vol. 1-3, Cold Spring Harbor Laboratory Press, Cold Spring Harbor, N.Y., 1989. The term recombinant includes nucleic acid molecules that have been altered solely by addition, substitution, or deletion of a portion of the nucleic acid molecule. Similarly, a recombinant protein can be encoded for by a recombinant nucleic acid molecule, or generated using chemical synthesis.

Replicative fitness: The ability of a pathogen to produce mature infectious progeny. In some examples, functionally deleting one or more genes of a pathogen reduces the replicative fitness of the pathogen, as compared to a pathogen containing a native gene sequence. In particular examples, functionally deleting one or more genes (such as two or more, for example two, three, four or five genes) in *F. tularensis*, such as two or more of dsbB, FTT0742, pdpB, fumA, and carB, reduces the replicative fitness of *F. tularensis*, as compared to *F. tularensis* containing native gene sequences. In some examples, such replicative fitness is reduced by at least 10%, such as at least 20%, at least 50%, or even at least 90% as compared to a *F. tularensis* containing native gene sequences.

Methods that can be used to determine replicative fitness are disclosed herein and are known in the art. For example, to determine the replicative fitness of a bacterium, exemplary replicative fitness assays include assays for colony-forming activity (for example see Example 2), assays that measure survival of a mammal into which the bacterium was introduced (see Example 3), reduced ability of the bacteria to survive various stress conditions (such as nutrient deprivation), altered host range, enzymatic assays indicating reduced activity of a key enzyme, or assays for reduced pathogenicity due to decreased expression of an important protein (such as LPS).

Specific Binding Agent: An agent that binds substantially only to a defined target. Thus a protein-specific binding agent binds substantially only the defined protein, or to a specific region within the protein. As used herein, a specific binding agent includes antibodies and other agents that bind substantially to a specified peptide.

The determination that a particular agent binds substantially only to a specific peptide can readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Specifically bind: Refers to the ability of a particular agent (a "specific binding agent") to specifically react with a particular analyte, for example to specifically immunoreact with an antibody, or to specifically bind to a particular peptide sequence. The binding is a non-random binding reaction, for example between an antibody molecule and an antigenic determinant. Binding specificity of an antibody is typically determined from the reference point of the ability of the antibody to differentially bind the specific antigen and an unrelated antigen, and therefore distinguish between two different antigens, particularly where the two antigens have unique epitopes. An antibody that specifically binds to a particular epitope is referred to as a "specific antibody".

In particular examples, two compounds are said to specifically bind when the binding constant for complex formation between the components exceeds about $10^4$ L/mol, for example, exceeds about $10^6$ L/mol, exceeds about $10^8$ L/mol, or exceeds about $10^{10}$ L/mol. The binding constant for two components can be determined using methods that are well known in the art.

Subject: Living multi-cellular organisms, a category that includes human and non-human mammals, as well as other veterinary subjects such as fish, non-human primates, cows, and birds.

Therapeutically effective amount: An amount of a therapeutic agent (such as an immunogenic composition) that alone, or together with an additional therapeutic agent(s), induces the desired response, such as a protective immune response or therapeutic response to a pathogen (such as *F. tularensis*). In one example, it is an amount of immunogen (such as attenuated *F. tularensis* having a functional deletion in one or more of dsbB, FTT0742, pdpB, fumA, or carB) needed to increase resistance to, prevent, ameliorate, or treat infection and disease caused by a pathogenic infection in a subject. Ideally, a therapeutically effective amount of an immunogen provides a therapeutic effect without causing a substantial cytotoxic effect in the subject. The preparations disclosed herein are administered in therapeutically effective amounts.

In general, an effective amount of a composition administered to a human or veterinary subject will vary depending upon a number of factors associated with that subject, for example whether the subject previously has been exposed to the pathogen. An effective amount of a composition can be determined by varying the dosage of the product and measuring the resulting immune or therapeutic responses, such as the production of antibodies. Effective amounts also can be determined through various in vitro, in vivo or in situ immunoassays. The disclosed therapeutic agents can be administered in a single dose, or in several doses, as needed to obtain the desired response. However, the effective amount of can be dependent on the source applied, the subject being treated, the severity and type of the condition being treated, and the manner of administration.

The disclosed therapeutic agents can be administered alone, or in the presence of a pharmaceutically acceptable carrier, or in the presence of other agents, for example an adjuvant.

In one example, a desired response is to increase an immune response in response to infection with a pathogen (such as *F. tularensis*). For example, the therapeutic agent can increase the immune response by a desired amount, for example by at least 5%, at least 10%, at least 15%, at least 20%, at least 25%, at least 30%, at least 50%, at least 75%, or even at least 90%, for example as compared to an immune response in the absence of the therapeutic agent. This increase can result in decreasing or slowing the progression of a disease or condition associated with a pathogenic infection (such as tularemia).

Treating a disease: Treatment refers to a therapeutic intervention that ameliorates a sign or symptom of a disease or pathological condition related to a disease (such as tularemia), even if the underlying pathophysiology is not affected. Reducing a sign or symptom associated with a pathogenic infection can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. For example, treatment of tularemia may be evidenced by a reduction or delayed onset of one or more of the following symptoms: fever, headache, chills and rigors, generalized body aches, coryza, sore throat, coughing, diarrhea, nausea, vomiting, anorexia, malaise, or weight loss.

Treatment can also induce remission or cure of a condition, such as a pathogenic infection or a pathological condition associated with such an infection (such as tularemia). In particular examples, treatment includes preventing a disease, for example by reducing or even avoiding altogether the full development of a disease or condition, such as a disease associated with a pathogen, such as tularemia. Thus, prevention of pathogenic disease can include reducing the number of subjects who acquire a disease associated with a pathogenic infection (such as the development of tularemia by *Francesella*) in a population of subjects receiving a preventative treatment (such as vaccination) relative to an untreated control population, or delaying the appearance of such disease in a treated population versus an untreated control population. Prevention of a disease does not require a total absence of disease. For example, a decrease of at least 50% can be sufficient.

Tularemia: The disease caused by infection with *Francesella* species, such as *F. tularensis*. The primary clinical forms of tularemia can vary in severity and presentation according to virulence of the infecting organism and the site of inoculum. Primary disease presentations include ulceroglandular, glandular, oculoglandular, oropharyngeal, pneumonic, typoidal, and septic forms. The onset of tularemia is usually abrupt, with symptoms that can include fever (38-40° C.), headache, chills and rigors, generalized body aches, coryza, sore throat, and coughing. Some subjects also experience diarrhea, nausea, or vomiting. As the disease progresses, subjects can experience sweats, fever, chills, progressive weakness, malaise, anorexia, and weight loss. If left untreated, symptoms often persist for several weeks. In ulceroglandular tularemia, a local cutaneous papule appears that the inoculation site at about the same time as the general symptoms. The papule ulcerates in a few days, and regional lymph nodes may become enlarged. Tularemia pneumonia, usually the result of inhaling *F. tularensis*, can be associated with pharyngitis, bronchiolitis, pleuropneumonitis, and hilar lymphadenitis.

Unit dose: A physically discrete unit containing a predetermined quantity of an active material calculated to individually or collectively produce a desired effect such as an immunogenic effect. A single unit dose or a plurality of unit doses can be used to provide the desired effect, such as an immunogenic effect. In one example, a unit dose includes a desired amount of one or more of the disclosed attenuated *F. tularensis* bacteria.

Vaccine: An immunogenic composition that can be administered to a veterinary subject or a human to confer immunity, such as active immunity, to a disease or other pathological condition (such as tularemia). Vaccines can be used therapeutically, for example prophylactically. Thus, vaccines can be used reduce the likelihood of infection or to reduce the severity of symptoms of a disease or condition or limit the progression of the disease or condition. In one example, a vaccine includes one or more of the disclosed attenuated *F. tularensis* bacteria.

Vector: A nucleic acid molecule as introduced into a host cell (such as a *F. tularensis* bacterial cell), thereby producing a transformed host cell. In particular examples, a vector includes nucleic acid sequences that permit allelic replacement of dsbB, FTT0742, pdpB, fumA, or carB in a *Francisella* cell. A vector can transduce, transform or infect a cell, thereby causing the cell to express nucleic acid molecules or proteins other than those native to the cell. A vector optionally includes materials to aid in achieving entry of the nucleic acid into the cell, such as a viral particle, liposome, protein coating or the like.

Attenuated *Francisella* Bacterium

The present disclosure provides isolated *Francisella* bacteria having functional deletions of one or more of the following genes: dsbB, FTT0742, pdpB, fumA, and carB. Such functional deletions attenuate the *Francisella* bacterium in an amount sufficient to significantly reduce or prevent the attenuated *Francisella* bacterium from evoking severe clinical symptoms in the subject, while allowing limited replication and growth of the bacteria in the recipient to produce an immune response in a subject.

In some examples, the *Francisella* bacterium is live. One skilled in the art will appreciate that the disclosed functional mutations can be made to any genus or variety of *Francisella*. In particular examples, the disclosed attenuated *Francisella* bacterium is *Francisella tularensis*, such as *Francisella tularensis* subspecies *tularensis* or *Francisella tularensis* subspecies *novicida*. In a specific example, the attenuated bacterium is *Francisella tularensis* subspecies *tularensis* strain SCHU S4.

In particular examples, at least 2, at least 3, at least 4, or all 5 of the dsbB, FTT0742, pdpB, fumA, and carB genes are functionally deleted in *Francisella*. One skilled in the art will appreciate that additional genes can also be functionally deleted, wherein the additional genes may or may not provide additional attenuation to the bacterium. Particular examples of combinations of genes that can be deleted are provided in Table 1. However, based on the teachings herein, those skilled in the art can determine other appropriate combinations.

TABLE 1

Exemplary combinations of functional deletions in *Francisella*.*

| | dsbB | FTT0742 | pdpB | fumA | carB |
|---|---|---|---|---|---|
| 1. | x | | | | |
| 2. | | x | | | |
| 3. | | | x | | |
| 4. | | | | x | |
| 5. | | | | | x |
| 6. | x | x | x | | |
| 7. | x | x | | | |

TABLE 1-continued

Exemplary combinations of functional deletions in *Francisella*.*

| | dsbB | FTT0742 | pdpB | fumA | carB |
|---|---|---|---|---|---|
| 8. | | x | x | | |
| 9. | x | | x | | |
| 10. | x | x | x | x | |
| 11. | x | x | x | x | x |
| 12. | x | x | x | | x |
| 13. | x | x | | x | |
| 14. | | x | x | x | |
| 15. | x | | | x | |
| 16. | | | x | x | |

*"X" in the box indicates gene is functionally deleted

Methods of Functionally Deleting Genes

As used herein, a "functionally deleted" or "inactivated" gene means that the gene has been mutated by insertion, deletion, or substitution (or combinations thereof) of one or more nucleotides such that the mutation substantially reduces (and in some cases abolishes) expression or biological activity of the encoded gene product. The mutation can act through affecting transcription or translation of the gene or its mRNA, or the mutation can affect the peptide gene product itself in such a way as to render it substantially inactive.

Functional deletion or one or more genes (which in some examples is also referred to as gene inactivation) can be performed using any conventional method known in the art. In one example, a strain of *Francisella* bacteria is transformed with a vector which has the effect of downregulating or otherwise inactivating the gene. This can be done by mutating control elements such as promoters and the like which control gene expression, by mutating the coding region of the gene so that any protein expressed is substantially inactive, or by deleting the gene entirely. For example, a gene can be functionally deleted by complete or partial deletion mutation (for example by deleting a portion of the coding region of the gene) or by insertional mutation (for example by inserting a sequence of nucleotides into the coding region of the gene, such as a sequence of about 1-5000 nucleotides). In particular examples, an insertional mutation includes introduction of a sequence that is in multiples of three bases (e.g. a sequence of 3, 9, 12, or 15 nucleotides) to reduce the possibility that the insertion will be polar on downstream genes. For example, insertion or deletion of even a single nucleotide that causes a frame shift in the open reading frame, which in turn can cause premature termination of the encoded peptide or expression of an substantially inactive peptide. Mutations can also be generated through insertion of foreign gene sequences, for example the insertion of a gene encoding antibiotic resistance.

In one example, functional deletion is achieved by deletion of a portion of the coding region of the dsbB, FTT0742, pdpB, fumA, or carB gene. Deletion mutations reduce the risk that the mutant will revert to a virulent state. For example, some, most (such as at least 50%) or virtually the entire coding region can be deleted. In particular examples, about 5% to about 100% of the gene is deleted, such as at least 20% of the gene, at least 40% of the gene, at least 75% of the gene, or at least 90% of the gene is deleted.

Figure 6:
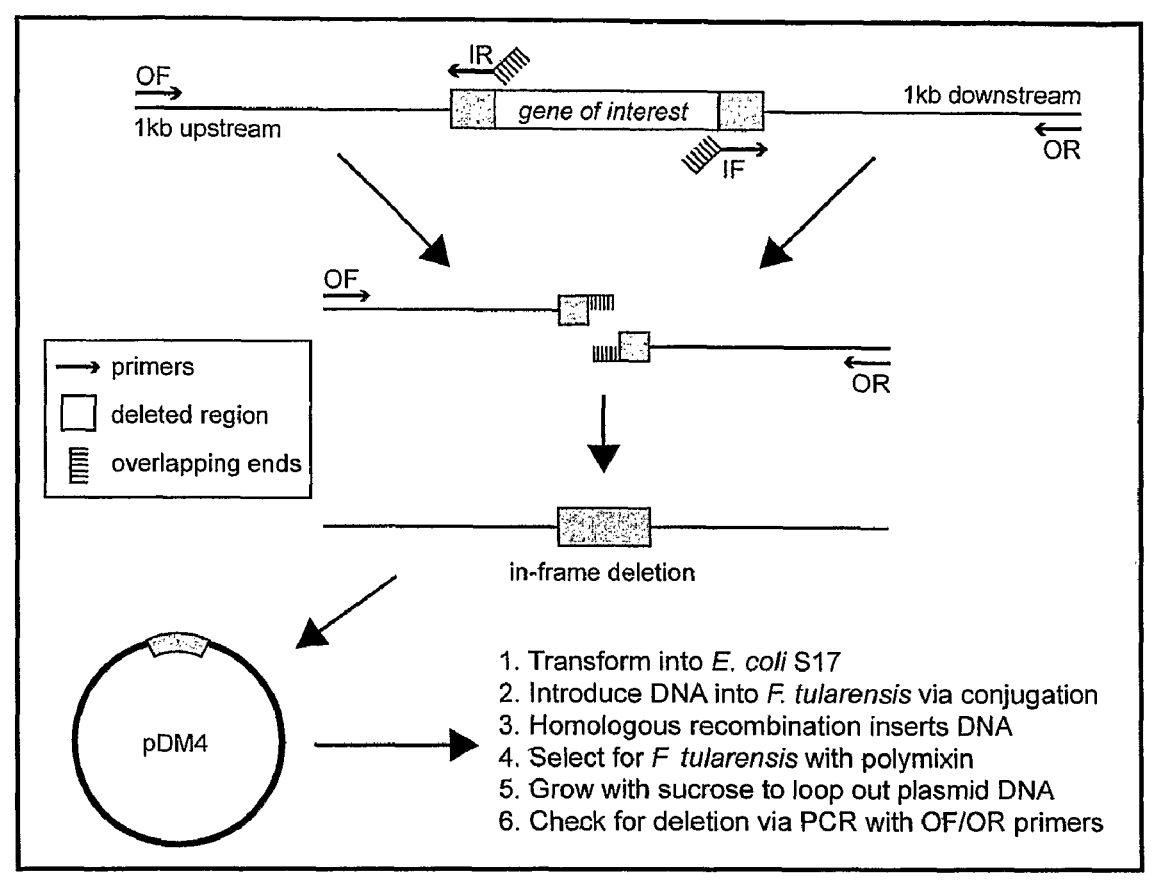

Deletion mutants can be constructed using any of a number of techniques known in the art. In one example, allelic exchange is employed to functionally delete one or more genes in *Francisella* (for example using the methods of Golovliov et al., *FEMS Microbiol. Lett.* 222:273-80, 2003). A specific example of such a method is shown in FIG. 6. A construct that includes the flanking region of the gene to be deleted with an in-frame deletion of a significant part of the gene is introduced into a pDM4 vector. This is a suicide vector in *F. tularensis*. In particular examples, pDM4 includes an antibiotic resistance marker, such as Kan$^r$. In particular examples, the resulting vector is transformed into *E. coli* strain S17. The resulting transformed *E. coli* is mated with a native *Francisella* bacteria (such as a wild-type virulent strain), thereby allowing the vector to be introduced into the *Francisella* bacteria via conjugation. The pDM4 vector DNA is incorporated into the *F. tularensis* genome by recombination between the homologous gene sequences. Conjugants can be selected based on the antibiotic resistance marker, such as selection with kanamycin (and for *F. tularensis* only with polymixin that kills *E. coli*). pDM4 also contains sacB, which does not permit r growth in/on sucrose. By growing the conjugants with sucrose, the incorporated plasmid DNA will loop out of the *F. tularensis* genome and leave behind one copy of the gene. PCR can be used to confirm if it is the deletion or the full-length wild-type copy. This results in an avirulent strain of *F. tularensis* that carries a deletion in dsbB, FTT0742, pdpB, fumA, or carB (or combinations thereof) and is antibiotic sensitive.

In one example, a strategy using counterselectable markers can be employed which has been utilized to delete genes in many bacteria. For a review, see, for example, Reyrat et al. (*Infec. Immun.* 66:4011-7, 1998). In this technique, a double selection strategy is often employed wherein a plasmid is constructed encoding both a selectable and counterselectable marker, with flanking DNA sequences derived from both sides of the desired deletion. The selectable marker is used to select for bacteria in which the plasmid has integrated into the genome in the appropriate location and manner. The counterselecteable marker is used to select for the very small percentage of bacteria that have spontaneously eliminated the integrated plasmid. A fraction of these bacteria will then contain only the desired deletion with no other foreign DNA present.

In another technique, the cre-lox system is used for site specific recombination of DNA. The system includes 34 base pair lox sequences that are recognized by the bacterial cre recombinase gene. If the lox sites are present in the DNA in an appropriate orientation, DNA flanked by the lox sites will be excised by the cre recombinase, resulting in the deletion of all sequences except for one remaining copy of the lox sequence. Using standard recombination techniques, the targeted gene of interest (dsbB, FTT0742, pdpB, fumA, carB, or combinations thereof) can be deleted in the *Francisella* genome and to replace it with a selectable marker (for example a gene coding for kanamycin resistance) that is flanked by the lox sites. Transient expression (by electroporation of a suicide plasmid containing the cre gene under control of a promoter that functions in *Francisella* of the cre recombinase should result in efficient elimination of the lox flanked marker. This process will produce a mutant containing the desired deletion mutation and one copy of the lox sequence.

In another method, a gene sequence in the *Francisella* genome is replaced with a marker gene, such as green fluorescent protein (GFP), β-galactosidase, or luciferase. In this technique, DNA segments flanking a desired deletion are prepared by PCR and cloned into a suicide (non-replicating) vector for *Francisella*. An expression cassette, containing a promoter active in *Francisella* and the appropriate marker gene, is cloned between the flanking sequences. The plasmid is introduced into wild-type *Francisella*. Bacteria that incorporate and express the marker gene are isolated and examined for the appropriate recombination event (replacement of the wild type gene with the marker gene).

Measuring Attenuation

Methods of determining whether functional deletion of one or more of dsbB, FTT0742, pdpB, fumA, or carB in *Francisella* attenuates the bacteria, for example in a mammal, are known in the art. Although particular examples are disclosed herein, the methods are not limiting. For example, attenuation of bacteria can be measured in vitro by infecting macrophages (such as a primary macrophage culture or a tissue culture cell line, for example those available from American Type Culture Collection, Manassas, Va.) with the mutated *Francisella* bacteria (for example containing functional deletions as shown in Table 1). In particular examples, cells are infected with a multiplicity of infection (MOI) of about 1-5000, such as an MOI of at least 1, at least 10, at least 100, at least 500, at least 1000, or at least 2000, for example an MOI of about 10-100, 1000-2000, or 500-1500. The MOI is the ratio of bacteria to the number of cells being infected, and thus is dependent on the number of macrophages present, but not necessarily the number that get infected. After the desired incubation, such as 12-48 hours (for example 24 hours), the macrophages are lysed and the resulting lysate cultured. The resulting growth of *Francisella* is monitored, for example by visual inspection of bacterial colonies. In particular examples, parallel reactions are performed for native *Francisella* bacteria of the same species and strain as the mutated bacteria. Mutated *Francisella* bacteria that exhibit smaller colonies or fewer colonies (such as an absence of colonies), for example as compared to a reference value representing native *Francisella* bacteria growth of the same species and strain, indicates that the mutated *Francisella* bacteria are attenuated. Such attenuated *Francisella* bacteria can be selected for further analysis, for example by determining attenuation in vivo.

Attenuation in vivo can be determined in a laboratory animal, such as a rodent (for example a mouse, rat, or rabbit) or non-human primate. Mutated *Francisella* bacteria are administered to the laboratory animal. A parallel set of animals can be administered native *Francisella* bacteria of the same species and strain as the mutated bacteria as a control. In particular examples, the animals are administered a dose of bacteria that is at least 50 times, such as at least 100 times, the $LD_{50}$ of the native bacteria in that animal. For example, for a mutated *Francisella tularensis* subsp. *tularensis*, mice can be administered $10^3$ to $10^{11}$ cfu bacteria, and rhesus monkeys can be administered $10^3$ to $10^{11}$ cfu bacteria. Any method of administration can be used, such as injection (for example intraperitoneal or intradermeal) or inhalation. The animals are subsequently observed for survival. Animals receiving *Francisella* bacteria containing one or more functional deletions in dsbB, FTT0742, pdpB, fumA, or carB, that exhibit 100% survival one month following infection, is an indication that the animal received an attenuated form of the *Francisella* bacteria. Such attenuated *Francisella* bacteria can be selected for further analysis. In contrast, animals administered the same dose of the native *Francisella* bacteria should demonstrate substantially 0% survival.

Measuring Immune Response

*Francisella* bacteria having a functional deletion of one or more of dsbB, FTT0742, pdpB, fumA, or carB that have been shown to be attenuated in vitro, in vivo, or both, can be examined for their ability to stimulate an immune response, for example to protect a subject from challenge with the native bacteria. Such methods are known in the art. For example, an immunogenic response of an animal to a composition that includes the attenuated *Francisella* bacteria disclosed herein can be evaluated indirectly through measurement of antibody titers or lymphocyte proliferation assays, or directly through monitoring signs and symptoms after challenge with wild type strain.

For example, the ability of *Francisella* bacteria having a functional deletion of one or more of dsbB, FTT0742, pdpB, fumA, or carB to stimulate an immune response can be determined following administration of the mutated bacteria to a subject (such as a human or laboratory animal) (for example using the methods described above). Subsequently, stimulation of the immune response can be measured. In one example, 7-60 days following administration of the *Francisella* bacteria having the desired functional deletions, a biological sample (such as blood or a fraction thereof, for example serum) can be obtained from the subject, and analyzed by an immunoassay (such as an ELISA or western blot) to determine the presence of antibodies against *Francisella* bacteria. For example, commercially available antibodies that specifically recognize one or more *Francisella* antigens (such as Mouse Anti-Francisella tularensis LPS Monoclonal Antibody from Abcam, Cambridge, Mass. and GeneTex, San Antonio, Tex.) can be contacted with a biological sample. In one example, microagglutination using formalin-inactivated bacteria as an antigen is used to detect the presence of *Francisella* antibodies in the biological sample. In a particular example, subjects having an antibody titer of $\geq 1:80$ are considered responders, while subjects having an antibody titer of $\leq 1:20$ are considered non-responders. In another example, stimulation of the immune response can be measured by detecting levels of cytokines in a biological sample obtained from the subject following administration of the bacteria. For example, levels of IL-6 and TNF-α can be measured using commercially available kits. In one example, an at least 5-fold increase (such as at least a 6-, 7-, 8-, 9- or 10-fold increase) in the level of IL-6 or TNF-α relative to background (or relative to an amount present before administration of the *Francisella* bacteria), indicates that the subject has had an immune response.

The immunogenic response of an animal to a composition that includes the attenuated *Francisella* bacteria disclosed herein can be evaluated directly through monitoring signs and symptoms after challenge with a native *Francisella* strain. For example, the ability of *Francisella* bacteria having a functional deletion of one or more of dsbB, FTT0742, pdpB, fumA, or carB to protect a subject from challenge with the native bacteria can be determined following administration of the mutated bacteria to a laboratory animal (for example using the methods described above). Any method of administration can be used, such as the methods described herein. Subsequently, for example 2-6 weeks (such as 4-6 weeks), the animal is administered native *Francisella* bacteria of the same subspecies and strain as the attenuated bacteria previously administered. The amount of native *Francisella* bacteria administered can be at least 1000 times the $LD_{50}$ observed for native infection, such as at least 5000 times, or at least 10,000 times the $LD_{50}$. The animals are subsequently observed for survival. Animals receiving *Francisella* bacteria containing one or more functional deletions in dsbB, FTT0742, pdpB, fumA, or carB, that exhibit 100% survival 7-28 days following challenge, indicates that the attenuated bacteria provides a protective immune response to the subject. Such attenuated *Francisella* bacteria can be selected for further analysis, for example human clinical trials. In contrast, animals not administered the attenuated *Francisella* bacteria should demonstrate substantially 0% survival.

Immunogenic Compositions

Immunogenic compositions are provided that include the disclosed attenuated *Francisella* bacteria. In particular examples, an immunogenic composition includes more than one type of attenuated *Francisella* bacteria. For example, the composition can include two or more populations of attenuated *Francisella* bacteria, such as the *Francisella* bacteria of groups 7 and 16 in Table 1. One skilled in the art will recognize that other combinations can be selected. In particular examples, the attenuated *Francisella* bacteria are present in a therapeutically effective amount.

The disclosed immunogenic compositions can include other biologically inactive or active agents (or both). For example, the disclosed immunogenic compositions can include adjuvants, carriers, excipients, anti-microbial agents (such as antibiotics), as well as pharmaceutically acceptable carriers (such as sterile water, saline, and preservatives).

For example, an immunogenic composition that includes the disclosed attenuated *Francisella* bacteria can also include one or more adjuvants. Adjuvants are agents that can augment the resultant immune response. Particular examples of adjuvants include, but are not limited to: Freund's Incomplete Adjuvant (IFA), Freund's complete adjuvant, and oil-emulsions.

In another example, an immunogenic composition that includes the disclosed attenuated *Francisella* bacteria can also include a pharmaceutically acceptable carrier. For example, a pharmaceutically acceptable carrier can be used to provide a medium in which to administer the composition into a subject. Exemplary pharmaceutical carriers include physiological saline, glycerol, and preservatives.

In some examples, an immunogenic composition that includes the disclosed attenuated *Francisella* bacteria can include both a pharmaceutically acceptable carrier and an adjuvant.

The immunogenic compositions can be packaged in forms convenient for delivery. The compositions can be enclosed within a capsule, caplet, sachet, cachet, gelatin, paper, or other container. In particular examples, dosage units are packaged, in tablets, capsules, suppositories or cachets. In particular examples, the disclosed immunogenic compositions are in a lyophilized form.

Methods of Stimulating an Immune Response

Methods are provided for eliciting an immune response against *Francisella* in a subject. In particular examples, the method includes administering to the subject a therapeutically effective amount of the attenuated *Francisella* bacteria disclosed herein (for example in the form of an immunogenic composition), thereby eliciting an immune response against *Francisella* in the subject. In particular examples, stimulating an immune response is used to treat tularemia in a subject previously infected with *Francisella tularensis* subsp. *tularensis* Type A or Type B. In other particular examples, stimulating an immune response is used to prevent development of tularemia in a subject who may become infected or has been infected with *Francisella tularensis* subsp. *tularensis* Type A or Type B.

In particular examples, the subject is a mammal, such as a laboratory animal (for example a mouse, rat, non-human primate, or rabbit), or human subject.

Methods of administration are known in the art. Particular examples of administration that can be used to practice the disclosed methods include, but are not limited to: injection (such as intradermal or subcutaneous), intranasal, transdermal, or oral administration. If desired, multiple administrations can be performed over time (for example by the administration of booster doses). In one example, one, two, or three additional administrations are performed, for example 1-6 months apart.

A "therapeutically effective amount" of the attenuated mutant *Francisella* bacteria is an amount effective to induce an immunogenic response in the recipient. In some examples, the immunogenic response is adequate to inhibit (including prevent) or ameliorate signs or symptoms of disease, including adverse health effects or complications thereof, caused by infection with wild type *Francisella* bacteria. Either humoral immunity or cell-mediated immunity or both can be induced by the attenuated mutant *Francisella* bacteria (for example in an immunogenic composition) disclosed herein.

The therapeutically effective amount can vary depending on the particular attenuated *Francisella* bacterium administered, the age, weight, or health of the subject, and other factors known to those skilled in the art. Ideally, the therapeutically effective amount produces a therapeutic immune response in the subject (for example by treating an existing *Francisella* infection or reducing the pathological consequences of a future *Francisella* infection), without significantly affecting the overall health of the subject.

In some examples, a therapeutically effective dose can be determined by also making reference to the $LD_{50}$ and $ED_{50}$ values for the attenuated bacterium. In one example, a therapeutically effective dose is 100-1000 fold less than the $LD_{50}$, and/or is at lest the $ED_{50}$ dose.

In a specific example, the therapeutically effective amount includes at least 50 colony forming units (cfu) of the attenuated *Francisella* bacterium, such as at least 100 cfu, at least 200 cfu, at least 300 cfu, at least 500 cfu, at least 800 cfu, at least 1000 cfu, for example 100 cfu to 500 cfu, or 100 cfu to 1000 cfu, of the attenuated *Francisella* bacteria. In other particular examples, depending on the route of administration, suitable amounts of the mutant bacteria to be administered include about $10^3$ to $10^{11}$ bacteria, such as $10^6$ to $10^{10}$, $10^8$ to $10^{10}$, or $10^9$ to $10^{10}$ attenuated *Francisella* bacteria.

Methods of determining whether an immune response has been generated can be determined using routine methods, such as indirect immunoassays or by direct clinical evaluation of the subject (for example by monitoring one or more signs of tularemia), for example as described above.

Example 1

Transposon Mutagenesis of *F. novicida*

This example describes methods used to mutagenize the *F. novicida* genome. Although this example describes methods using *F. novicida*, similar methods can be used to mutagenize any *Francisella* species, such as *F. tularensis*.

*F. novicida* strain U112 (Fran Nano, University of Victoria) was cultured at 37° C. in tryptic soy broth supplemented with 0.1% cysteine (TSBC; Becton, Dickinson and Company [BD], Sparks, Md.) or on cysteine heart agar (CHA; Difco/BD) plates. Kanamycin was added to a final concentration of 20 µg/ml to these media for selection of U112 strains carrying the transposon (TSBC/Kan20 or CHA/Kan20).

To generate a library of *F. novicida* transposon insertion mutants, mini-Tn5 transposon/transposase complexes were electroporated into appropriately prepared *F. novicida*. The transposase/transposon complex completes the transposition event once inside the bacteria. The method used was similar to that of Kawula et al. (Kawula et al., *Appl. Environ. Microbiol.* 70:6901-4, 2004). The mini-Tn5-cycler transposon was constructed as previously described (Geddes et al., *Infect. Immun.* 73:6260-71, 2005). The transposon/transposase complex was prepared as described by Goryshin et al. (Goryshin et al., *Nat. Biotechnol.* 18:97-100, 2000).

*F. novicida* U112 was grown to confluency on CHA plates at 37° C. Bacteria scraped from a single plate were resuspended with 5 ml of ice-cold 10% glycerol/500 mM sucrose, and 1 ml aliquots were transferred to 1.5 ml microcentrifuge tubes. The bacteria were washed in the glycerol/sucrose solution and pelleted at 12K×g for 5 minutes at 4° C. The supernatant was then discarded. This wash step was repeated for a total of 4 washes. After the final wash, each aliquot was resuspended in 100 µl buffer. One microliter of transposon/transposase complex was added to each tube. After transferring the bacteria/DNA mixture to 1 mm gap electroporation cuvettes on ice, the samples were electroporated at 1.5 to 1.7 kV, 200 Ω, 25 μf. The bacteria were recovered in 1 ml TSBC in glass tubes for 4 hours in a 37° C. rotator. Transformants were selected by plating on CHA/Kan20 plates.

These transposon mutagenesis methods yielded as many as 150 transposon mutants from a single electroporation procedure.

Example 2

Screening and Identification of Disrupted Loci

This example describes methods used to screen the resulting library of more than 700 *F. novicida* transposon mutants for those that exhibited a reduced ability to grow in macrophages. Macrophages were used because the primary host cell type for *Francisella* in both humans and animals is the macrophage (Fortier et al., *Immunol. Ser.* 60:349-61, 1994).

To identify those *F. novicida* mutants attenuated for growth in macrophages, macrophages were individually infected with overnight bacterial cultures as follows. The RAW264.7 and J774A.1 murine macrophage cell lines (American Type Culture Collection [ATCC], Manassas, Va.) were cultured in Dulbecco's modification of Eagle's medium (DMEM; Gibco-BRL, Rockville, Md.) supplemented with 10% fetal bovine serum (FBS; Gibco-BRL), 1 mM non-essential amino acids (Gibco-BRL), and 0.2 mM sodium pyruvate (Gibco-BRL) at 37° C. with 5% $CO_2$. The THP-1 human macrophage cell line (ATCC) was cultured in Roswell Park Memorial Institute (RPMI; Gibco-BRL) 1640 and differentiated in RPMI with 200 ng/ml phorbol myristate acetate (PMA; Sigma Chemical, St. Louis, Mo.). For infections, bacterial cultures were added to 50% confluent macrophages in 24- or 96-well culture dishes (Corning, Corning, N.Y.) or 4-chamber microscope plates (Nalge Nunc, Naperville, Ill.) at a multiplicity of infection (MOI) of approximately 1000, and the cells were centrifuged at 1K×g for 5 minutes at room temperature and incubated at 37° C. with 5% $CO_2$. One hour post-infection, adherent macrophages were washed twice with phosphate-buffered saline (PBS), and either DMEM (J774 and RAW cells) or RPMI (THP-1 cells) containing 100 μg/ml of gentimicin was added to prevent the growth of any extracellular bacteria. Two hours post-infection, macrophages were washed twice with PBS, and either DMEM or RPMI containing 10 μg/ml gentimicin was added. The infections were then incubated at 37° C. with 5% $CO_2$ for 24 hours.

To lyse the RAW and J774 macrophages, 0.5% saponin (Sigma) in TSBC was added to each well followed by incubation for 30 minutes at 37° C. with 5% $CO_2$. THP-1 macrophages were simply lysed in distilled deionized water ($ddH_2O$). After lysing the macrophages, an equal amount of each lysate (3%) was spotted onto CHA/Kan20 plates and incubated overnight at 37° C. Those strains that exhibited reduced growth in macrophages were identified visually by smaller or absent areas of growth.

To eliminate those strains that were simply defective in overall growth, RAW macrophages were again infected in 24-well plates, as above, with an input MOI of 100. After lysing the macrophages, 10% of each lysate (50 μl) was spread onto CHA plates and incubated overnight at 37° C. The lysates were examined visually, and *F. novicida* mutants with fewer colonies than the wild-type U112 control were identified to be defective for growth in macrophages.

Of more than 700 *F. novicida* transposon mutants screened, 34 exhibited reduced growth in RAW macrophages. Sequences for 28 of these mutant strains (Table 2) were determined using the method described by Geddes et al. (*Infect. Immun.* 73:6260-71, 2005). Briefly, chromosomal DNA from *F. novicida* mutants exhibiting reduced growth in macrophages was prepared, digested with EcoRI, and subcloned into pACYC184. Ligation reactions were electroporated into chemically competent GeneHogs *E. coli* cells (Invitrogen) in LB broth at 37° C., according to manufacturer's directions. Colonies containing the transposon were selected for by growth at 37° C. on LB plates containing 60 μg/ml kanamycin (LB/Kan60). Plasmids from kanamycin-resistant colonies were purified according to the manufacturer's instructions using the QIAprep Spin miniprep kit (Qiagen, Valencia, Calif.). The DNA sequence of the fusion junction was obtained using a primer complementary to base pairs 166-190 of the 5' end of mini-Tn5-cycler (5' GTTGACCAGGCGGAACATCAATGTG 3'; SEQ ID NO: 1). Sequence analysis was performed using MacVector™ 7.2.3 software and the NCBI Blast server available on the Internet.

TABLE 2

*F. novicida* transposon mutant strains generated

| Mutant | Corresponding SchuS4 FTT | Gene disrupted | % identity to SCHU S4[a] | Nucleotide location of Tn insert[b] | % survival rate[c] |
|---|---|---|---|---|---|
| 1 | FTT0107c | dsbB | 100 | 114151 | 100 |
| 2 | FTT0145 | rpoC | 99 | 163108 | 0 |
| 3 | FTT0203c | purH | 99 | 222340 | 100 |
| 4 | FTT0334 | rpsQ | 100 | 342324 | 0 |
| 5 | FTT0356 | htpG | 95 | 356504 | 100 |
| 6 | FTT0504c | sucC | 97 | 524250 | 0 |
| 7 | FTT0583 | fopA | 98 | 599781 | 0 |
| 8 | FTT0742 | hypothetical[d] | 89 | 765155 | 100 |
| 9 | FTT0893 | purM | 98 | 901556 | 100 |
| 10 | FTT0893 | purM | 97 | 901647 | 100 |
| 11 | FTT0893 | purM | 98 | 901848 | 100 |
| 12 | FTT0894 | purCD | 99 | 904045 | 100 |
| 13 | FTT0894 | purCD | 99 | 904160 | 100 |
| 14 | FTT0917 | maeA | 98 | 926193 | 33 |
| 15 | FTT1165c | aspC2 | 99 | 1179264 | 0 |
| 16 | FTT1222 | dedA2 | 98 | 1240288 | 33 |
| 17 | FTT1241 | glyA | 97 | 1261475 | 67 |
| 18 | FTT1269c | dnaK | 100 | 1291446 | 100 |
| 19 | FTT1345/1700 | pdpB[e] | 98 | 1384141/1777485 | 100 |
| 20 | FTT1369c | tktA | 97 | 1416905 | 100 |
| 21 | FTT1535c | ocd | 99 | 1597434 | 0 |
| 22 | FTT1535c | ocd | 97 | 1597841 | 0 |
| 23 | FTT1600c | fumA | 98 | 1667516 | 100 |
| 24 | FTT1629c | hypothetical[f] | 99 | 1692570 | 0 |
| 25 | FTT1664 | carB | 99 | 1730805 | 100 |
| 26 | FTT1720c | purL | 98 | 1804171 | 100 |

TABLE 2-continued F. novicida transposon mutant strains generated

| Mutant | Corresponding SchuS4 FTT | Gene disrupted | % identity to SCHU S4[a] | Nucleotide location of Tn insert[b] | % survival rate[c] |
|---|---|---|---|---|---|
| 27 | FTT1720c | purL | 97 | 1805882 | 100 |
| 28 | FTT1769c | clpB | 96 | 1858564 | 0 |

[a] using the fragment sequence
[b] corresponding to SCHU S4
[c] at 7 days after infection with $6 \times 10^3$ cfu, groups of 3 mice
[d] lipoprotein
[e] SCHUS4 contains two copies of pdpB
[f] membrane protein

Example 3

F. novicida Mutants Exhibit Attenuation in Mice

This example describes methods used to identify the F. novicida mutants obtained in Example 2 that would retain an attenuated phenotype in a mammal. One skilled in the art will appreciate that similar methods can be used to identify other Francisella mutants (such as those having one or more functionally deleted genes) that retain an attenuated phenotype in any mammal.

To identify those mutant strains that retained an attenuated phenotype in an animal model, wild-type BALB/c mice were infected with the 28 F. novicida mutants that were attenuated for growth in macrophages (Table 2). Mice (7- to 8-week old female BALB/c mice, Jackson Laboratory, Bar Harbor, Me.) were injected intraperitoneally (i.p.) with $6 \times 10^3$ bacteria in 150 μl of PBS, which is about 100 times greater than the wild-type F. novicida $LD_{50}$ in mice. Groups of three mice were infected with $6 \times 10^3$ colony forming units (cfu) of the 28 attenuated mutants (Table 2). Control groups of three mice were infected with $6 \times 10^2$ and $6 \times 10^3$ cfu F. novicida U112.

At 4 weeks post-infection, 16 of the insertion mutants provided 100% mouse survival, indicating that those mutants were highly attenuated (Table 2).

Example 4

F. novicida Mutants Protect Mice Against Challenge

This example describes methods used to determine which of the 16 attenuated F. novicida transposon mutants identified in Example 3 could confer protection against wild-type infection.

These 48 surviving vaccinated mice were challenged with $8 \times 10^5$ cfu of wild-type F. novicida U112 four weeks after infection with mutant F. novicida strains. This dose is greater than 10,000 times the $LD_{50}$ observed for wild-type infection.

As shown in Table 3, at 7 days post-infection, 5 of the 16 mutants demonstrated 100% protection after a single vaccination: those with transposon insertions in dsbB, the ORF corresponding to FTT0742 (henceforth referred to as FTT0742), pdpB, fumA, and carB. In contrast, wild-type control infections led to 0% survival.

TABLE 3

F. novicida transposon mutants attenuated in mice

| F. novicida mutants | % Survival[a,b] |
|---|---|
| dsbB | 100 |
| purH | 0 |
| htpG | 0 |
| FTT0742 | 100 |
| purM | 0 |
| purM | 0 |
| purM | 33 |
| purCD | 0 |
| purCD | 0 |
| dnaK | 0 |
| pdpB | 100 |
| tktA | 66 |
| fumA | 100 |
| carB | 100 |
| purL | 0 |
| purL | 33 |

[a] After challenge with $8 \times 10^5$ wild-type U112
[b] Groups of 3 mice, injected intraperitoneally These results demonstrate that these five F. novicida transposon mutants are significantly attenuated in a mouse infection model in comparison to the wild-type parental strain, and provide protection to subsequent F. novicida infection. Interestingly, there was a lack of protection conferred by pur mutants in a murine model. It has been previously postulated that mutations affecting the F. tularensis purine synthesis pathway could be used to generate a live attenuated tularemia vaccine (Karlsson et al., Microb. Comp. Genomics 5:25-39, 2000). Although the F. novicida transposon library contained eight unique pur mutants: purA, a purCD fusion (2 strains), purL (2 strains), and purM (3 strains), each of which exhibited 100% attenuation in mice with $6 \times 10^3$ cfu, all of them failed to protect against a wild-type parental challenge with $8 \times 10^5$ cfu. Therefore, the purine biosynthesis mutants did not confer as high level of protection as the other F. novicida transposon mutant strains.

Example 5

Determination of F. novicida Mutant $LD_{50}$

This example describes methods used to calculate the 50% lethal dose ($LD_{50}$) of the five protective strains identified in Example 4 (Table 3). One skilled in the art will appreciate that similar methods can be used to determine $LD_{50}$ for any Francisella mutant containing one or more functionally deleted genes.

The $LD_{50}$ values were calculated according to the method of Reed and Muench (Am. J. Hyg. 27:493-7, 1935). Briefly, groups of five mice were infected i.p. with $5 \times 10^5$, $5 \times 10^6$, and $5 \times 10^7$ cfu of the five protective mutant strains (Table 3). A control group was also infected with $6 \times 10^3$ cfu of F. novicida U112. Surviving mice were challenged 28 days later with $6 \times 10^7$ cfu F. novicida U112. Infection with the mutant strains was repeated with groups of 5 mice at the following doses: $6 \times 10^1$, $6 \times 10^2$, and $6 \times 10^3$ cfu for U112; $6 \times 10^5$, $6 \times 10^6$, and $6 \times 10^7$ cfu for dsbB; $6 \times 10^7$ cfu for FTT0742; $6 \times 10^7$ cfu for pdpB; $6 \times 10^4$, $6 \times 10^5$, and $6 \times 10^6$ cfu for fumA; $6 \times 10^3$, $6 \times 10^4$, and $6 \times 10^5$ cfu for carB. Mice were checked for signs of illness or death twice each day following infection.

The F. novicida U112 parental strain was observed to have an $LD_{50}$ of 66.25 cfu (Table 4). The carB mutant exhibited the least attenuation with an $LD_{50}$ of $6.75 \times 10^3$ cfu. The $LD_{50}$ values for dsbB and fumA mutants were $6.625 \times 10^5$ cfu and $6.17 \times 10^5$ cfu, respectively. The mutant strains with the highest level of attenuation in an animal infection model were FTT0742 and pdpB, both of which were observed to have $LD_{50}$ values of >6×10$^7$ cfu.

TABLE 4

| LD$_{50}$ of five protective *F. novicida* mutants | |
|---|---|
| Strain | LD$_{50}$[a] |
| wild-type U112 | 66.25 |
| dsbB | 6.625 × 10$^5$ |
| FTT0742 | >6 × 10$^7$ |
| pdpB | >6 × 10$^7$ |
| fumA | 6.17 × 10$^5$ |
| carB | 6.75 × 10$^3$ |

[a]In cfus, intraperitoneal infection

Example 6

*F. novicida* Mutants are Highly Attenuated for Growth in Macrophages

This example describes methods used to determine the amount of attenuation of the *F. novicida* mutants in mammalian macrophages.

To calculate the level of attenuation in macrophages, wild-type *F. novicida* U112 and the five mutants (Table 4) that conferred protection were quantified for growth in multiple macrophage cell lines. RAW, J774, and the human macrophage cell line THP-1 were seeded to 50% confluency in 24-well tissue culture plates and infected in triplicate with an input MOI of 100 for 24 hours (see Example 2). Macrophages were lysed with 0.5% saponin in TSBC at 24 hours post-infection. Serial dilutions of the lysates were plated onto CHA/Kan20 (mutants) or CHA (wild-type and mock infection controls) plates. After overnight incubation at 37° C., the colonies on each plate were counted and cfu/ml was calculated and converted to log scale. Means and standard deviations were calculated using Microsoft Excel X for Mac.

As shown in FIGS. 1A-C, each of the mutant strains (dsbB, FTT0742, pdpB, fumA, and carB) was significantly impaired for growth in the J774 and RAW mouse macrophage cell lines (FIGS. 1A and 1B). With the exception of the fumA mutant, these strains also exhibited attenuation in the THP-1 human macrophage cell line (FIG. 1C). The fumA gene encodes fumarate hydratase A, the component of the Kreb's cycle (citric acid cycle/CAC) that converts fumarate to malate. This metabolic pathway is necessary for generating energy and provides precursory molecules for compounds such as amino acids (Tseng et al., *J. Bacteriol.* 183:461-7, 2001). Thus, the apparent disparity of fumA attenuation in J774 and RAW versus THP-1 macrophages could be attributed to simple metabolic differences between mice and humans in the intracellular availability of fumarate and/or malate. Only the pdpB mutant strain exhibited a defect in the ability to enter macrophages (colonies counted at 2 hours p.i.).

Example 7

Infection with *F. novicida* Mutants does not Reduce Host Cell Integrity

This example describes methods used to demonstrate that the observed attenuation phenotypes described in Example 6 were not the result of increased host cell killing. Increased host cell killing would yield less live infected macrophages and thus fewer overall bacteria upon quantification.

One method for determining the degree of cytotoxicity that results from bacterial infection is to measure cell lysis, which can be assessed via the release of the stable cytosolic enzyme lactate dehydrogenase (LDH) using the method of van der Velden et al. (*Infect. Innnun.* 68:5702-9, 2000). Briefly, J774 macrophages seeded in 96-well culture plates were infected in triplicate with either one of the five transposon mutants or wild-type *F. novicida* U112 at an input MOI of 100. After 48 hours, the supernatants were removed and assayed for released LDH using the CytoTox 96 Non-Radioactive Cytotoxicity Assay (Promega, Madison, Wis.). Cytotoxicity was determined for each mutant strain by calculating the LDH released as a percentage of the maximal release from macrophages infected with wild-type U112.

As shown in FIG. 2, the five mutant strains are significantly impaired in their abilities to cause cell lysis in comparison with wild-type *F. novicida*. With the levels of LDH released during wild-type infection normalized to 100%, the LDH released from infection with the five attenuated mutants ranged from 9.75% (FTT0742) to 24.52% (fumA). These results indicate that the attenuation phenotypes are not due to increased killing of the host cell by the transposon mutants and that these strains are indeed compromised for intracellular replication.

Example 8

Attenuated Mutants do not Exhibit Major In Vitro Growth Defects

This example describes methods used to demonstrate that the reduced growth phenotype of the five *F. novicida* mutant strains (dsbB, FTT0742, pdpB, fumA, and carB) was not attributed to an overall defect in their abilities to replicate.

A growth curve was determined for each mutant. Briefly, overnight cultures of each *F. novicida* were diluted into 10 ml of TSBC to an optical density at 600 nm ($OD_{600}$) of 0.1. Optical density readings were then recorded at the specified timepoints. Cultures were diluted 1:10 for $OD_{600}$>1 for accuracy. It was previously determined by plating that $OD_{600}$ 1≈4×10$^9$ bacteria/ml.

As shown in FIG. 3, the FTT0742, pdpB, and dsbB mutants replicated at levels similar to that of wild-type U112. The fumA and carB mutants may have some defects in replication, as was observed by their divergence from the other strains after four hours of growth in liquid media. However, these two mutants were not compromised in their abilities to enter host cells. Thus, it is unlikely that this difference in replication is wholly responsible for the attenuated and protective phenotypes observed in macrophages and mice and do not prevent these mutants as potential immunogens.

Example 9

Each *F. novicida* Mutant Harbors a Single Transposon

Transposon mutagenesis has the potential to yield strains with multiple transposon insertions. This example describes Southern methods used to demonstrate that the attenuation phenotype each of the five protective *F. novicida* transposon mutants were the result of a single transposition event.

To quantify the number of inserts, a DNA probe that spans the unique HindIII site in the transposon was designed. Hence, digestion of chromosomal DNA harboring a single transposon insert yields two targets for this probe. *F. novicida* chromosomal DNA was prepared using the CTAB (cetyltrimethylammonium bromide) method (Ausubel, F. M. 2002. Short protocols in molecular biology: a compendium of methods from Current protocols in molecular biology, 5th ed. Wiley, New York), and 250 ng of each preparation were digested to completion with HindIII. Digested DNA was run on a 0.8% agarose gel for 2 hours at 90 kV and then transferred to a positively charged nylon membrane (Roche) using a standard capillary transfer method. DNA was crosslinked to the membrane at 120,000 µjoules/cm² using the Stratalinker 1800 UV Crosslinker (Stratagene, La Jolla, Calif.). The digested bacterial DNA was probed with a digoxigenin (DIG) labeled probe that was prepared using the DIG High Prime DNA Labeling and Detection Starter Kit II (Roche, Indianapolis, Ind.). By using a DNA probe that spans a HindIII site in the transposon and therefore hybridizes to two separate locations of the HindIII-digested chromosomal DNA, the number of transposon insertions in each strain was determined. The fragments harboring the transposon were detected according to manufacturer's instructions with the DIG High Prime DNA Labeling and Detection Starter Kit II (Roche). The membrane was exposed to film (Kodak, Rochester, N.Y.) for 2 or 8 minutes.

Each *F. novicida* mutant strain was confirmed to harbor a single copy of the transposon insert as indicated by the presence of two bands.

Example 10

Replication of *F. novicida* Mutant Strains in Macrophages

This example describes fluorescence microscopy methods used to visually assess the replication of *F. novicida* transposon mutants in macrophages.

J774 macrophages were infected and prepared for microscopy as follows. J774 macrophages were infected at an input MOI of 100 with one of each of the five mutants in 4-well chamber plates (Nalge Nunc). After 24 hours, the cells were washed twice with PBS, fixed for 1 hour with 4% paraformaldehyde, and stored in PBS at 4° C. After washing 3×10 min in PBS, the cells were permeabilized with 0.5% Triton X-100 (Sigma Chemical) in PBS for 20 minutes at room temperature. The cells were then blocked with 5% FBS in PBS for 30 minutes and incubated for one hour at 4° C. with a polyclonal antibody that recognizes *F. tularensis* (BD). After washing 3×10 minutes in PBS, the cells were again blocked with 5% FBS. A goat-anti-rabbit antibody conjugated to Alexa 488 (Molecular Probes, Eugene, Oreg.) was applied to the cells overnight at 4° C. The cells were once again washed 3×10 min in PBS and incubated with a 1:1000 dilution of FM 4-64 membrane stain (Molecular Probes) and 1:000 Draq5 DNA stain in PBS (Alexis Biochemicals, San Diego, Calif.) for 10 minutes at room temperature. The cells were washed twice with PBS, mounted in Fluormount-G® antifade solution (Southern Biotechnology, Birmingham, Ala.), and imaged with an Applied Precision DeltaVision Deconvolution microscope system (Advanced Precision Instruments, Issaquah, Wash.). All images were taken using a 60× objective. Stacks of 10 Z plane images spaced 1 micron apart were captured at 1024×1024 pixels and deconvolved for seven iterations.

Macrophages infected with *F. novicida* U112 contained a greater number of bacteria compared to those cells infected with the *F. novicida* mutants. Although multiple fumA mutants were observed inside host cells, infections with the dsbB, FTT0742, pdpB, and carB mutant strains resulted in only one or two intracellular bacteria at 24 hours p.i. These observations confirm that the *F. novicida* transposon mutants are defective for replication inside macrophages. Furthermore, although the macrophages were initially seeded at the same concentration, fewer cells remained after infection with wild-type U112 when compared to the mutants and uninfected controls. This indicates that host cell death occurred during the course of the infection, further supporting the LDH assay results that macrophages infected with *F. novicida* U112 are more prone to cell death than those infected with the mutant strains.

Example 11

*F. novicida* Mutants Disseminated within the Body are Cleared

This example describes methods used to demonstrate that *F. novicida* mutants disseminated to the liver, spleen, and lungs were subsequently cleared.

Ideally, vaccine candidates infect mice transiently and are cleared before challenge with the parent strain. BALB/c mice (15) were inoculated i.p. with 0.1 $LD_{50}$ (in 150 µl total volume) of each of the five *F. novicida* mutants. Thus, for these infections, the vaccination dose varied from strain to strain. Three mice from each group were sacrificed at 1, 3, 5, 7, and 28 days after vaccination, and their spleen, liver, and lungs harvested. The organs were homogenized using a stomacher, and plated in serial dilutions.

As shown in FIGS. 4A-E, each mutant, with the possible exception of carB mutant, disseminated to all three organs from the original site of inoculation. Two of the five strains (dsbB and fumA mutants) were completely cleared by day 28 following infection. Although relative low numbers of bacteria remained in the spleen at day 28 after infection with FTT0742 and pdpB mutants, it is possible that these organisms would have been cleared in

TABLE 6

Primers that can be used to amplify genes of *F. tularensis**

| | Primer Sequence | SEQ ID NO: |
|---|---|---|
| dsbB | | |
| OF | GGGCCCTGGCGCCGTTAGAGATATGTT | 2 |
| IF | CCCATGTGTAAATCAATCACCGGAACAATC | 3 |
| IR | GGTGATTGATTTACACATGGGACATGGTTTCCAA | 4 |
| OR | GTCGACATTTGCATATGTTGCTTGAACA | 5 |
| FTT0742 | | |
| OF | CTCGAGATGGTATAGATACACCCCAGCCAG | 6 |
| IF | ATTGCTTTAGTTGGCTGCGGTTATATTCCACACA CGGCGAACG | 7 |
| IR | GTTCGCCGTGTGTGGAATATAACCGCAGCCAACTAA AGCAAT AGGTAG | 8 |
| OR | AGATCTACCCTGATCTATCCAACGTGATGG | 9 |
| pdpB | | |
| OF | CTCGAG AGCACTTTGGACTAAGCACAAACC | 10 |
| IF | CAAAGACCATAAAAAATGCATGTACCTGGGTAATC AAGCACAAAG | 11 |

TABLE 6-continued

Primers that can be used to
amplify genes of F. tularensis*

| | Primer Sequence | SEQ ID NO: |
|---|---|---|
| IR | TGCTTGATTACCCAGGTACATGCATTTTTTATGGTC TTTGAGGCAG | 12 |
| OR | AGATCTCCAACCATTGTTGCTGTAGAACC | 13 |
| fumA | | |
| OF | CTCGAG GCTCACCAATTAGTGACCATCCTC | 14 |
| IF | AAAGTTTAGGACCTTGCTGATCACGCTGATATGCTT CATACATTG | 15 |
| IR | TATGAAGCATATCAGCGTGATCAGCAAGGTCCTAA ACTTTGGAAAC | 16 |
| OR | AGATCTAATTAGCGAGGTTGGCAAGAGGAG | 17 |

*OF = outer forward, IF = inner forward, IR = inner reverse, OR = outer reverse. Upper arm of gene cloned with OF and IR, downstream arm cloned with IF and OR. OF and OR used in the second PCR reaction to connect the two arms and to engineered restriction sites into the OF and OR primers (OF has XhoI and OR has XbaI, except for dsbB has ApaI on OF and SalI on OR). In some examples, the engineered restriction sites are not needed, for example if the PCR products are cloned into an intermediate vector (pCR-Blunt-II-TOPO, Invitrogen) and cut out with restriction sites on the vector (such as XhoI and SpeI, except for FTT0742, which uses XhoI and BamHI on the TOPO vector and XhoI and BglII on pDM4 due to SpeI sites in the FTT0742 ORF).

The resulting PCR product is cleaned (for example gel purified using the Qiagen Qiaex kit) and cloned into an intermediate vector, such as pGEM T-Easy (Promega). Once in pGEM, the deletion fragment can be cut out using ApaI and XhoI (whose sites are engineered into the outer primers) and cloned into the pDM4 vector (modified to be kanamycin resistant and chloramphenicol sensitive by adding a full Kan cassette and the vaccinations because a lower dose (10-1,000-fold fewer bacteria) was used (Tables 3 and 5).

Example 12

Expressing Full-Length Genes in Trans Complemented the Attenuation Phenotype

This example describes methods used to demonstrate that each mutant derivative could be complemented by expressing cloned copies of the genes.

The dsbB gene was amplified from SCHU S4 DNA by PCR and cloned into plasmid pKK202. Following transformation into the dsbB mutant, the abilities to replicate within macrophages and cause disease in mice were determined. The levels of entry (2 hours) and replication (24 hours) were determined for wild-type strain U112, the dsbB mutant, and the dsbB mutant complemented with pKK202-dsbB in the J774 and RAW cell lines, and in primary BMDM. Entry and replication rates in RAW cells were determined for complementation of the FTT0742 and fumA mutants.

Figure 5:
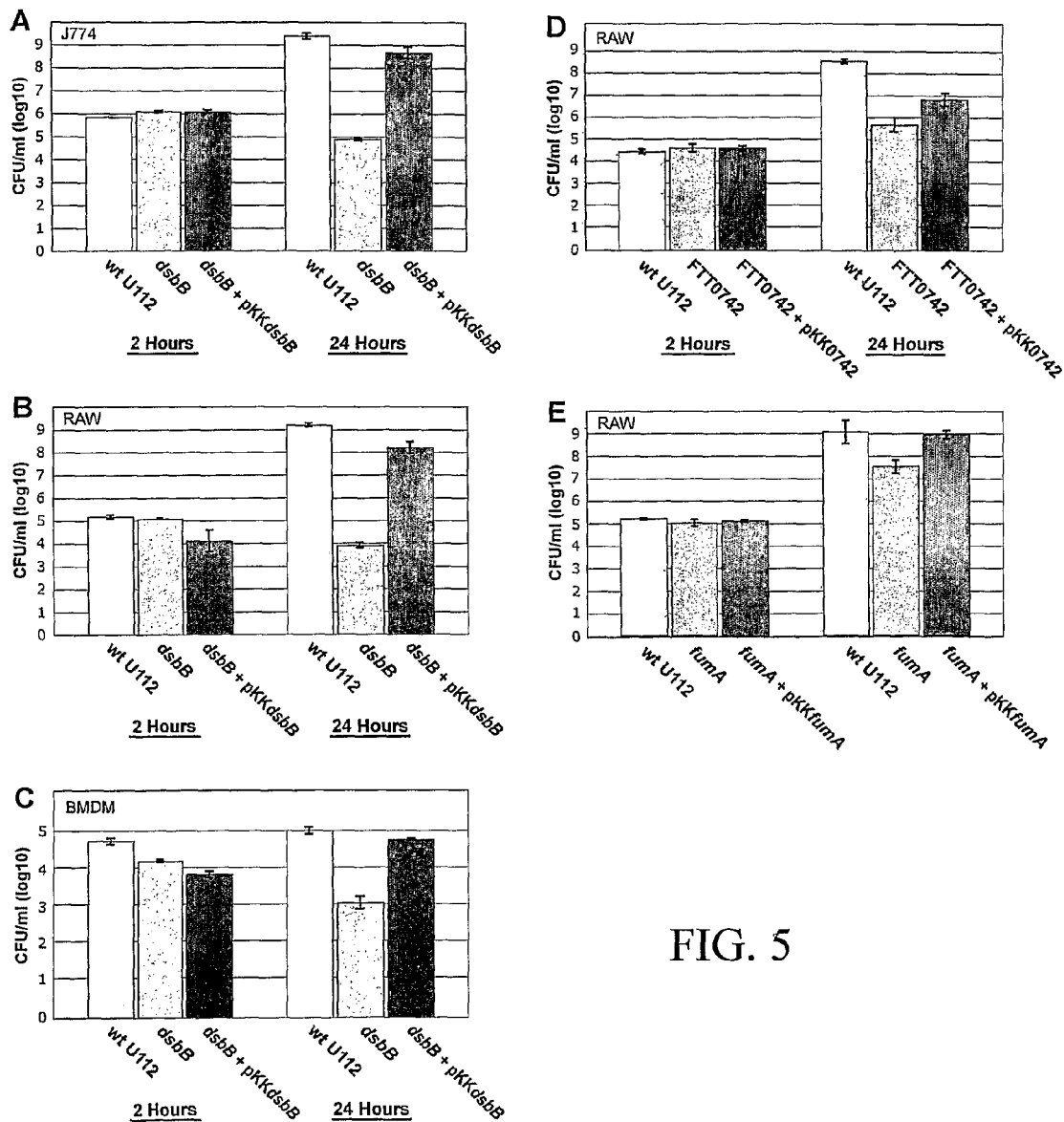
FIGS. 5A-E are bar graphs showing that expression of full-length genes in trans complements the attenuation defects of (A-C) dsbB, (D) FTT0742, and (E) fumA, in (A) J744, (B, D, E) RAW, and (C) BMDM cells. Each column shows the average for three separate infections.

As shown in FIGS. 5A-C, in trans expression of the cloned dsbB gene provided nearly complete complementation of the virulence defect in three different cell types. The $LD_{50}$ was 60.25 CFU, which is comparable to the wild-type $LD_{50}$ (66.25 CFU).

In trans expression of the full-length FTT0742 gene in the corresponding mutant derivative resulted in incomplete complementation. In RAW cells, intracellular replication of the complemented FTT0742 strain was 10-fold greater than intracellular replication of the mutant, but the value was still nearly 2 orders of magnitude less than the wild-type value (FIG. 5D).

Complementation of the fumA mutation with the full-length gene restored the level of intracellular growth to the level of wild-type *F. novicida* (FIG. 5E).

These results demonstrate that the observed attenuation phenotypes were due to mutation in dsbB, FTT0742 and fumA.

Example 13

Protection of Mice Against Very High Doses of Wild-Type Bacteria

This example describes methods used to assess the level of protection afforded by the dsbB, FTT0742, pdpB, fumA, and carB *F. novicida* transposon insertion mutants in vivo.

Vaccinated mice were challenged with higher doses of the wild-type U112 parental strain. Each mutant strain (dsbB, FTT0742, pdpB, fumA, and carB) was used to separately infect groups of five mice with doses of $6 \times 10^5$, $6 \times 10^6$, and $6 \times 10^7$ cfu (see Table 5). Mice infected with each of the three doses of the FTT0742 and pdpB mutants had a 100% survival rate, as did mice infected with the lowest doses of the dsbB and fumA mutants. Conversely, infections with the carB strain resulted in 0% survival. Four weeks after vaccination, surviving animals were challenged with $6 \times 10^7$ cfu of wild-type *F. novicida* U112, which is approximately 1 million-fold the observed $LD_{50}$ for wild-type infection. All of the challenged mice survived without any symptoms of tularemia.

TABLE 5

Challenge studies after vaccination with
F. novicida transposon mutants

| Mutant strain | Vaccine dose (cfu) | % Survival (5 mice) | Challenge dose (cfu) | % Survival |
|---|---|---|---|---|
| dsbB | $6 \times 10^5$ | 100 | $6 \times 10^7$ | 100 |
| | $6 \times 10^6$ | 20 | $6 \times 10^7$ | 100 |
| | $6 \times 10^7$ | 0 | ND | ND |
| FTT0742 | $6 \times 10^5$ | 100 | $6 \times 10^7$ | 100 |
| | $6 \times 10^6$ | 100 | $6 \times 10^7$ | 100 |
| | $6 \times 10^7$ | 100 | $6 \times 10^7$ | 100 |
| pdpB | $6 \times 10^5$ | 100 | $6 \times 10^7$ | 100 |
| | $6 \times 10^6$ | 100 | $6 \times 10^7$ | 100 |
| | $6 \times 10^7$ | 100 | $6 \times 10^7$ | 100 |
| fumA | $6 \times 10^5$ | 100 | $6 \times 10^7$ | 100 |
| | $6 \times 10^6$ | 0 | ND | ND |
| | $6 \times 10^7$ | 0 | ND | ND |
| carB | $6 \times 10^5$ | 0 | ND | ND |
| | $6 \times 10^6$ | 0 | ND | ND |
| | $6 \times 10^7$ | 0 | ND | ND |

These results demonstrate that the dsbB, FTT0742, pdpB, and fumA transposon mutants are capable of protecting mice against infection with very high levels of the wild-type organism. Overall, the results indicate that *F. tularensis* strains carrying mutations in dsbB, FTT0742, pdpB, and fumA can be used in an immunogenic composition as a therapeutic against tularemia.

Example 14

*F. tularensis* Immunogenic Compositions

As demonstrated in the Examples above, *F. novicida* mutants having a functionally deleted dsbB, FTT0742, pdpB, fumA, or carB gene can provide protection against challenge with *F. novicida*. Based on these teachings, immunogenic compositions derived from a virulent *Francisella* species, such as *F. tularensis* type A or type B, can be generated. In a particular example, the virulent *Francisella* species is *F. tularensis* subsp. *tularensis* (type A) strain SCHU S4 (available from the Centers for Disease Control). It is expected that functional deletions in one or more of dsbB, FTT0742, pdpB, fumA, or carB in any virulent *Francisella* species, such as *F. tularensis*, will provide a therapeutic effect. This is because all of the *F. tularensis* subspecies *are* closely related. For example, the 16S rDNA sequences of each are nearly identical, and their genomes share greater than 95% sequence identity, indicating that genes necessary for intracellular growth in *F. novicida* are likely to have the same function in *F. tularensis*. In addition, complementation experiments shown in FIGS. 5A-E were with SCHU S4 DNA, indicating that the genes are functionally conserved among the subspecies.

Although this example describes a particular method for functionally deleting the dsbB, FTT0742, pdpB, and fumA genes in *F. tularensis* subsp. *tularensis* (type A) strain SCHU S4 using allelic exchange, the disclosure is not limited to this method of gene inactivation, or to these genes and strain of bacteria. One skilled in the art using routine methods can make other functional deletions (such as those in Table 1) using other methods, for example in a *F. tularensis* subsp. *tularensis* (type B) strain.

The dsbB, FTT0742, pdpB, and fumA genes can be functionally deleted in *F. tularensis* subsp. *tularensis* (type A) strain SCHU S4 using the allelic exchange method of Goloviov et al. (*FEMS Microbiol. Lett.* 222:273-80, 2003, herein incorporated by reference as to the method) (see FIG. 6). Briefly, primers that recognize the dsbB, FTT0742, pdpB, and fumA genes of *F. tularensis* subsp. *tularensis* (type A) strain SCHU S4 and can amplify regions at either end of the gene plus about 1 kb of flanking DNA are generated using routine methods (see Table 6 for exemplary primers). The "internal" ends of the primers are designed such that the two products will overlap by about 20 bp. These PCR products are then used as a template for a second PCR reaction to generate one product containing the flanking regions of the gene with an in-frame deletion of much of the gene. deletion approx. 50% of the Cm gene with restriction enzyme digestion and ligation). pDM4 (see Milton et al., *J. Bacteriol.* 178:1310-9, 1996), is a suicide vector with a sacB gene that is lethal in the presence of sucrose. The pDM4 vector containing the deletion fragment is transformed into *E. coli* strain S17. Conjugation between S17 and *Francisella* is used to transfer the vector (overnight at 25° C. on LB plates). *Francisella* that contain the vector are selected for on McLeod plates containing polymixin (kills *E. coli*) and kanamycin (selects for pDM4). Resulting colonies are then screened for integration by PCR. Positive integrants are grown at 37° C. to log phase (OD600~0.6) in Chamberlain's medium, sucrose is added to the medium to a final concentration of 5%, and grown for one hour longer. The culture is spread onto McLeod plates containing 5% sucrose. Colonies are analyzed using PCR to confirm have the deletion (and have not resolved back to wild-type).

The resulting *F. tulensis* strains will each contain a deletion of one of the genes (dsbB, FTT0742, pdpB, fumA, or carB). In order to make particular combinations of deletions (e.g. deletion of 2, 3, 4, or 5 of the genes, for example see Table 1) these strains containing one functionally deleted dsbB, FTT0742, pdpB, fumA, or carB gene will undergo additional rounds of conjugation and selection to introduce one or more additional functional deletions.

The resulting *F. tularensis* subsp. *tularensis* (type A) strain containing a functional deletion in the dsbB, FTT0742, pdpB, or fumA gene (or combinations thereof), can be formulated into an immunogenic composition. In one example, the mutated attenuated bacteria are mixed with a pharmaceutically acceptable carrier, alone or in combination with an adjuvant. In a particular example, the bacteria are lyophilized and reconstituted with a sterile pharmaceutically acceptable carrier at the time of use. The immunological composition can be administered to a mammal, such as BALB/c mice, using the methods described in Examples 2-4, to demonstrate the bacteria are attenuated and provide a protective immune response (for example in response to an aerosol challenge). Similarly, the immunological composition can be administered to a mammal, such as a human, at a therapeutically effective dose to treat or prevent *Francisella* infection.

Example 15

Pharmaceutical Compositions

The disclosed attenuated *Francisella* mutants can be incorporated into pharmaceutical compositions (such as immunogenic compositions or vaccines). Any pharmaceutical composition provided herein can be prepared using well known methods.

Pharmaceutical compositions can include one or more *Francisella* bacteria containing functional deletions in one or more of dsbB, FTT0742, pdpB, fumA, or carB (for example see Table 1). Pharmaceutical compositions within the scope of the disclosure can include one or more other compounds, which can be either biologically active or inactive. Particular examples for other compounds include, but are not limited to, physiologically acceptable carriers, excipients, immunostimulants, or combinations thereof. The pharmaceutical compositions can also include preservatives, carbohydrates (such as glucose, mannose, sucrose or dextrans), mannitol, antioxidants, and chelating agents. In some examples, an immunostimulatory composition includes one or more adjuvants and one or more pharmaceutically acceptable carriers.

Immunostimulants

In particular examples, pharmaceutical compositions include an immunostimulant. An immunostimulant is any substance that enhances or potentiates an immune response to an exogenous antigen. Examples of immunostimulants include adjuvants, biodegradable microspheres (such as polylactic galactide microspheres) and liposomes (see, for example, U.S. Pat. No. 4,235,877). Any of a variety of immunostimulants can be employed in the pharmaceutical compositions that include an immunogenically effective amount of attenuated *Francisella*.

Adjuvants are non-specific stimulators of the immune system that can enhance the immune response of the host to the immunogenic composition. Some adjuvants contain a substance designed to protect the antigen from rapid catabolism, for example, aluminum hydroxide or mineral oil, and a stimulator of immune responses, such as lipid A, *Bordatella pertussis* or *Mycobacterium tuberculosis* derived proteins. Suitable adjuvants are commercially available as, for example, Merck Adjuvant 65 (Merck and Company, Inc., Rahway, N.J.), TiterMax Gold (TiterMax, Norcross, Ga.), ISA-720 (Seppic, France) ASO-2 (SmithKlineGlaxo, Rixensart, Belgium); aluminum salts such as aluminum hydroxide (for example, Amphogel, Wyeth Laboratories, Madison, N.J.) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and saponins such as quil A and QS-21 (Antigenics, Framingham, Mass.). Cytokines, such as GM-CSF or interleukin-2, -7, or -12, can be used as adjuvants.

The adjuvant composition can be designed to induce an immune response predominantly of the Th1 type. High levels of Th1-type cytokines (such as IFN-γ, TNF-α, IL-2 and IL-12) tend to favor the induction of cell mediated immune responses to an administered antigen. In contrast, high levels of Th2-type cytokines (such as IL-4, IL-5, IL-6 and M-10) tend to favor the induction of humoral immune responses. Following administration of a pharmaceutical composition as provided herein, a subject may support an immune response that includes Th1- and Th2-type responses. However, in examples where the response is predominantly a Th1-type, the level of Th1-type cytokines increases to a greater extent than the level of Th2-type cytokines. The levels of these cytokines can be readily assessed using standard assays.

Adjuvants for use in eliciting a predominantly Th1-type response include, but are not limited to, a combination of monophosphoryl lipid A, such as 3-de-O-acylated monophosphoryl lipid A (3D-MPL) (Corixa, Hamilton Ind.), together with an aluminum salt. MPL adjuvants are available from Corixa (Seattle, Wash.; see also U.S. Pat. Nos. 4,436,727; 4,877,611; 4,866,034 and 4,912,094). CG-containing oligonucleotides (in which the CG dinucleotide is unmethylated) also induce a predominantly Th1 response. Such oligonucleotides are well known and are described, for example, in PCT publications WO 96/02555 and WO 99/33488. Immunostimulatory DNA sequences are also described, for example, by Sato et al., *Science* 273:352, 1996. Another adjuvant is a saponin such as QS21 (Antigenics, Framingham, Mass.), which can be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other formulations include an oil-in-water emulsion and tocopherol. An adjuvant formulation involving QS21, 3D-MPL and tocopherol in an oil-in-water emulsion is described in WO 95/17210.

Still further adjuvants include Montanide ISA 720 (Seppic, France), SAF (Chiron, California, United States), ISCOMS (CSL), MF-59 (Chiron), the ASO-2 series of adjuvants (SmithKlineGlaxo, Rixensart, Belgium), Detox (Corixa, Seattle, Wash.), RC-529 (Corixa, Seattle, Wash.), Aminoalkyl glucosaminide 4-phosphates (AGPs), copolymer adjuvants, CG oligonucleotide motifs and combinations of CG oligonucleotide motifs, bacterial extracts (such as mycobacterial extracts), detoxified endotoxins, and membrane lipids. Still other adjuvants include polymers and co-polymers. For example, copolymers such as polyoxyethylene-polyoxypropylene copolymers and block co-polymers can be used. A particular example of a polymeric adjuvant is polymer P1005. Combinations of two or more adjuvants can be used in the pharmaceutical compositions provided herein.

Adjuvants are utilized in an adjuvant amount, which can vary with the adjuvant, subject, and immunogen. Typical amounts of non-emulsion adjuvants can vary from about 1 ng to about 500 mg per administration, for example, 10 μg to 800 μg, such as 50 μg to 500 μg per administration. For emulsion adjuvants (oil-in-water and water-in-oil emulsions) the amount of the oil phase can vary from about 0.1% to about 70%, for example about 0.5% to 5% oil in an oil-in-water emulsion and about 30% to 70% oil in a water-in-oil emulsion. Those skilled in the art will appreciate appropriate concentrations of adjuvants, and such amounts can be readily determined.

Pharmaceutically Acceptable Carriers

While any suitable carrier known to those of ordinary skill in the art can be employed in the pharmaceutical compositions, the type of carrier can vary depending on the mode of administration. Pharmaceutical compositions can be formulated for any appropriate manner of administration, including for example, oral (including buccal or sublingual), nasal, rectal, aerosol, topical, intravenous, intraperitoneal, intradermal, intraocular, subcutaneous or intramuscular administration. For parenteral administration, such as subcutaneous injection, exemplary carriers include water, saline, alcohol, glycerol, fat, wax, buffer (such as neutral buffered saline or phosphate buffered saline), or combinations thereof. For oral administration, any of the above carriers or a solid carrier can be employed. Biodegradable microspheres (such as polylactate polyglycolate) can also be employed as carriers for the pharmaceutical compositions. Suitable biodegradable microspheres are disclosed, for example, in U.S. Pat. Nos. 4,897,268 and 5,075,109.

Carriers for use with the disclosed compositions are biocompatible, and can also be biodegradable, and the formulation can provide a relatively constant level of active component release. Suitable carriers include, but are not limited to, microparticles of poly(lactide-co-glycolide), as well as polyacrylate, latex, starch, cellulose and dextran. Other delayed-release carriers include supramolecular biovectors, which comprise a non-liquid hydrophilic core (such as a cross-linked polysaccharide or oligosaccharide) and, optionally, an external layer comprising an amphiphilic compound, such as a phospholipid (see, for example, U.S. Pat. No. 5,151,254 and PCT publications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles can be employed with the disclosed pharmaceutical compositions to facilitate production of an antigen-specific immune response to *Francisella*. Exemplary vehicles include, but are not limited to, hydrophilic compounds having a capacity to disperse the attenuated *Francisella* bacteria and any additives. The attenuated bacteria can be combined with the vehicle according to methods known in the art. The vehicle can be a solvent or dispersion medium containing, for example, water, ethanol, polyol (for example, glycerol, propylene glycol, liquid polyethylene glycol, and the like), and suitable mixtures thereof. Other exemplary vehicles include, but are not limited to, copolymers of polycarboxylic acids or salts thereof, carboxylic anhydrides (for example, maleic anhydride) with other monomers (for example, methyl(meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof.

A biodegradable polymer can be used as a base or vehicle, such as polyglycolic acids and polylactic acids, poly(lactic acid-glycolic acid) copolymer, polyhydroxybutyric acid, poly(hydroxybutyric acid-glycolic acid) copolymer, and mixtures thereof. Other biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. In some examples, vehicles include synthetic fatty acid esters such as polyglycerin fatty acid esters and sucrose fatty acid esters. Hydrophilic polymers and other vehicles can be used alone or in combination, and enhanced structural integrity can be imparted to the vehicle by partial crystallization, ionic bonding, cross-linking and the like.

The vehicle can be provided in a variety of forms, including, fluid or viscous solutions, gels, pastes, powders, microspheres and films. In one example, pharmaceutical compositions for administering attenuated *Francisella* bacteria are formulated as a solution, microemulsion, or other ordered structure suitable for high concentration of active ingredients. Proper fluidity for solutions can be maintained, for example, by the use of a coating such as lecithin, by the maintenance of a desired particle size in the case of dispersible formulations, and by the use of surfactants.

Time Release Formulations

The disclosed compositions can be administered as part of a sustained release formulation (such as a capsule, sponge or gel that includes the attenuated *Francisella* bacteria) that provides a slow release of the composition following administration. These compositions can be prepared with vehicles that protect against rapid release, and are metabolized slowly under physiological conditions following their delivery (for example in the presence of bodily fluids). Many methods for preparing such formulations are well known to those skilled in the art (see, for example, Sustained and Controlled Release Drug Delivery Systems, J. R. Robinson, ed., Marcel Dekker, Inc., New York, 1978). Examples include, but are not limited to, a polymer, controlled-release microcapsules, and bioadhesive gels. For example, sustained-release formulations can contain attenuated *Francisella* bacteria dispersed in a carrier matrix or contained within a reservoir surrounded by a rate controlling membrane. In one example, a controlled-release formulation can be administered by, for example, subcutaneous implantation at the desired target site.

Packaging

Pharmaceutical compositions can be presented in unit-dose or multi-dose containers, such as sealed ampoules or vials. Such containers are typically hermetically sealed to preserve sterility of the formulation until use. In general, formulations can be stored as suspensions, solutions or as emulsions in oily or aqueous vehicles. In particular examples, the disclosed compositions are stored at temperatures from about 4° C. to −100° C. until use.

The pharmaceutical compositions of the disclosure typically are sterile and stable under conditions of manufacture, storage and use. Sterile solutions can be prepared by incorporating the disclosed attenuated *Francisella* bacteria (alone or in the presence of a pharmaceutically acceptable carrier or an adjuvant (or other biologically active agent) in the desired amount in an appropriate solvent followed by sterilization, such as by filtration, radiation, or heat. Generally, dispersions are prepared by incorporating the attenuated *Francisella* bacteria into a sterile vehicle that contains a dispersion medium and other desired ingredients. In the case of sterile powders, methods of preparation include vacuum drying and freeze-drying which yields a powder of the attenuated *Francisella* bacteria plus any additional desired ingredient from a previously sterile-filtered solution thereof. For vaccine use, the attenuated *Francisella* bacteria of the disclosure can be used directly in vaccine formulations, or lyophilized, as desired, using lyophilization protocols well known in the art. Lyophilized attenuated *Francisella* bacteria is typically be maintained at about 4° C. When ready for use the lyophilized attenuated *Francisella* bacteria can be reconstituted in a stabilizing solution (such as saline).

Example 16

Methods of Stimulating an Immune Response

This example describes methods using the disclosed immunogenic compositions (such as those described in Examples 14 and 15) that can be used to stimulate an immune response in a subject, such as a mammal, for example a human or veterinary subject.

Methods for inoculation are routine in the art. In some examples, a determination is made as to whether the subject would benefit from administration of the disclosed immunogenic compositions, prior to administering the immunogenic composition. For example, subjects who have been exposed or are likely to be exposed to a virulent form of *Francisella* can be selected to receive the immunogenic composition. Administration can be achieved by any method known in the art, such as oral administration, inhalation, or inoculation (such as intramuscular, ip, or subcutaneous). In some examples, the immunogenic composition includes live attenuated *Francisella* bacteria containing a functional deletion in one or more of the dsbB, FTT0742, pdpB, fumA, or carB genes (such as those listed in Table 1). In particular examples, attenuated *Francisella* bacteria are administered in the presence of other agents, such as an adjuvant or pharmaceutical carrier (or both).

The amount of live attenuated *Francisella* bacteria containing a functional deletion in one or more of the dsbB, FTT0742, pdpB, fumA, or carB genes administered is sufficient to induce in the host an effective immune response against virulent forms of *Francisella*. An effective amount can being readily determined by one skilled in the art, for example using routine trials establishing dose response curves. The immunogenic compositions disclosed herein can be administered to the subject as needed to confer immunity against *Francisella* to the subject. For example, the composition can be administered in a single bolus delivery (which can be followed by one or more booster administrations as needed), via continuous delivery over an extended time period, in a repeated administration protocol (for example, by an hourly, daily, weekly, or monthly repeated administration protocol).

In some examples, live attenuated *Francisella* bacteria containing a functional deletion in one or more of dsbB, FTT0742, pdpB, fumA, or carB gene are administered to a subject. In particular examples, the inactivated whole-cell vaccine is administered to the subject (for example orally, nasally, or via injection). Exemplary doses of bacteria (as measured by colony-forming units), include, but are not limited to, $10^3$-$10^{10}$ bacteria per dose, for example at least $10^3$ bacteria, at least $10^4$ bacteria, at least $10^5$ bacteria, at least $10^8$ bacteria, or at least $10^9$ bacteria per dose.

Provided below are particular examples of methods that can be used to stimulate an immune response in a mammalian subject. However, the disclosure is not limited to these particular examples.

Calculation of $LD_{50}$

The $LD_{50}$ for the desired attenuated *Francisella tularensis* bacterium containing a functionally deleted dsbB, FTT0742, pdpB, fumA, or carB gene (or combinations thereof) can be determined using methods known in the art. In one example, the method described in Example 5 is used. For example, increasing amounts of attenuated *Francisella tularensis* bacteria are administered to a laboratory animal (such as a mouse, rat, rabbit, or non-human primate), and the animal monitored for survival for up to 30 days. The mean time to death can be calculated by dividing the sum of the survival times of all animal by the total number of animals examined.

The dose of attenuated *Francisella tularensis* bacteria used to stimulate an immune response in a mammal (such as a human) is generally about 100 to 1000 fold lower than the calculated $LD_{50}$.

Administration of Live Bacteria

In one example, attenuated *Francisella tularensis* bacteria that include a functionally deleted dsbB, FTT0742, pdpB, fumA, or carB gene (or combinations thereof), are administered to a mammal, such as a veterinary subject or human, via scarification. For example, the bacteria can be administered as a single dose in about 0.1 ml by scarification to the forearms of a human. In particular examples, the dose of bacteria is about $10^6$-$10^8$ bacteria.

In another example, attenuated *Francisella tularensis* bacteria that include a functionally deleted dsbB, FTT0742, pdpB, fumA, or carB gene (or combinations thereof), are administered to a mammal, such as a veterinary subject or human, via aerosol. For example, the bacteria can be administered intranasally as a single dose in about 50-500 µl physiological saline. In particular examples, the dose of bacteria is about $10^3$ to $10^{10}$ bacteria.

In yet another example, attenuated *Francisella tularensis* bacteria that include a functionally deleted dsbB, FTT0742, pdpB, fumA, or carB gene (or combinations thereof), are administered to a mammal, such as a veterinary subject or human, via intradermal or subcutaneous injection. For example, the bacteria can be administered as a single dose in about 50 µl-1 ml physiological saline. In particular examples, the dose of bacteria is about $10^3$ to $10^7$ bacteria. In one example, mice are injected subcutaneously with 50 µl-100 µl of an inoculum containing about $10^3$ to $10^5$ bacterium in the flank or at the base of the tail.

Exemplary Assessment in Mice

In a particular example, wild-type mice (such as pathogen-free female BALB/c 8-12-week old, mice (Jackson Laboratory, Bar Harbor, Me.)) are used to demonstrate the efficacy of an attenuated *Francisella tularensis* bacteria that includes a functionally deleted dsbB, FTT0742, pdpB, fumA, or carB gene. Mice are intranasally administered an immunogenic composition containing live attenuated *Francisella tularensis* that have a functionally deleted dsbB, FTT0742, pdpB, fumA, or carB gene (or combinations thereof) (50 µl of immunogenic composition). Alternatively, the immunogenic composition can be administered intradermally into a fold of skin in the mid-belly utilizing a 26.5 gauge needle. If desired, mice can be anesthetized with isofluorane prior to administration of the immunogenic composition. Mice each are administered approximately $10^{10}$-$10^{11}$ $TCID_{50}$ (amount of bacteria required for 50% infectivity of susceptible cells in tissue culture) of live attenuated *Francisella tularensis* that have a functionally deleted dsbB, FTT0742, pdpB, fumA, or carB gene (or combinations thereof), or with phospho-buffered saline (PBS) as a negative control.

Subsequently, mice are administered wild-type virulent *F. tularensis* (such as type A or type B *F. tularensis*, for example type A strain FSC033). For example, 4-12 weeks following administration of the immunogenic composition, mice are challenged intradermally (for example administered into the base of the tail or into a fold of skin in the mid-belly) with about 10 cfu of virulent type A or type B strain of *F. tularensis* in phosphate-buffered saline and survival monitored. Alternatively, 4-12 weeks following administration of the immunogenic composition, mice are challenged intranasally (for example via a Lovelace nebulizer) with about 20 cfu of virulent type A or type B strain of *F. tularensis* and survival monitored.

All inoculated animals are observed daily for signs of tularemia (ruffled fur, inertia, or death). Blood can be collected from mice 15-30 days after infection (such as 21 days post infection). Serum samples are analyzed for the presence of neutralizing antibody to *F. tularensis*, using any standard immunoassay known to those skilled in the art. Blood will be collected before euthanasia when necessary.

Assessment in a Non-Human Primate Model

As an alternative to using mice to assess the efficacy of an immunogenic composition that includes live attenuated *Francisella* bacteria, the ability of such bacteria to be used as an immunogen can be determined in rhesus monkeys. The live attenuated *Francisella* bacteria disclosed herein can be administered to monkeys and the immune response assayed, for example using the methods described above for mice. Briefly, 2-4 juvenile rhesus monkeys are administered $10^3$-$10^{11}$ cfu of attenuated bacteria orally, intraperitoneally, or by aerosol. The ability of the attenuated *Francisella* bacteria to stimulate an immune response in the treated monkeys can be determined as described above.

Monkeys can be subsequently challenged with 1000×$LD_{50}$ of a virulent strain of a native *Francisella tularensis*.

Measurement of Immune Response

The following methods can be used to assess immunogenicity of the live attenuated *Francisella tularensis* that have a functionally deleted dsbB, FTT0742, pdpB, fumA, or carB gene (or combinations thereof). The presence of neutralizing antibodies can be assessed by testing serum samples obtained from the subject for the presence of antibodies to *F. tularensis*. For example, the microagglutination method of Bevanger et al. (*J. Clin. Microbiol.* 26:433-7, 1988, herein incorporated by reference) can be used to determine the antibody titer in the serum. In particular examples, antibody titers of ≧1:80 are considered responsive, while nonresponders have a titer of ≦1:20.

In another example, following immunization, sera is obtained from immunized and non-immunized subjects. For example, sera can be analyzed for the presence of specific neutralizing antibodies to *F. tularensis*, for example using an agglutination assay.

Production of specific neutralizing antibodies when inoculated with live attenuated *F. tularensis* that have a functionally deleted dsbB, FTT0742, pdpB, fumA, or carB gene (or combinations thereof) would give evidence of protective immunity.

Further evidence that attenuated *F. tularensis* bacteria provide protection from illness or death resulting from infection with *F. tularensis*, can be obtained from challenge studies. For example, following administration of the attenuated *F. tularensis* bacteria, animals are challenged with dosages of virulent *F. tularensis* sufficient to cause illness or death in unprotected laboratory animals (such as mice or monkeys), for example a dose equivalent to 100-1000 times the $LD_{50}$. The absence of signs of tularemia (or a decrease in the severity of such signs) or absence of death when challenged indicates that the laboratory animals are protected by their prior exposure to attenuated *F. tularensis* bacteria.

In view of the many possible embodiments to which the principles of the disclosure can be applied, it should be recognized that the illustrated embodiments are only examples of the disclosure and should not be taken as limiting the scope of the disclosure. Rather, the scope of the disclosure is defined by the following claims. We therefore claim as our invention all that comes within the scope and spirit of these claims.

We claim:

1. An isolated *Francisella* bacterium that can produce an immune response in a subject, wherein the *Francisella* bacterium comprises a functional deletion of one or more genes that attenuate the *Francisella* bacterium, wherein the genes comprise dsbB, FTT0742, pdpB, fumA, carB, or combinations thereof, and wherein the functional deletion attenuates the bacterium.

2. The isolated *Francisella* bacterium of claim 1, wherein the *Francisella* bacterium comprises a functional deletion of at least two genes.

3. The isolated *Francisella* bacterium of claim 1, wherein the FTT0742 gene, pdpB gene, or combinations thereof, is functionally deleted.

4. The isolated *Francisella* bacterium of claim 1, wherein the *Francisella* bacterium is a strain of *Francisella tularensis*.

5. The isolated *Francisella* bacterium of claim 1, wherein the *Francisella* bacterium is live.

6. The isolated *Francisella* bacterium of claim 1, wherein the one or more genes are functionally deleted by complete or partial deletion mutation or by insertional mutation.

7. An immunogenic composition comprising the isolated *Francisella* bacterium of claim 1.

8. The immunogenic composition of claim 7, further comprising an adjuvant.

9. The immunogenic composition of claim 7, further comprising a pharmaceutically acceptable carrier.

10. A method of eliciting an immune response against *Francisella* in a subject, comprising administering to the subject a therapeutically effective amount of the immunogenic composition of claim 7, thereby eliciting an immune response in the subject.

11. The method of claim 10, wherein administering comprises intranasal administration.

12. The method of claim 10, wherein the therapeutically effective amount comprises 100 to 1000 colony forming units (cfu) of the isolated *Francisella* bacterium.

13. A method of treating tularemia in a subject, comprising administering the immunogenic composition of claim 7 to the subject.

14. A method of treating infection by a *Francisella* species in a subject, comprising administering the isolated *Francisella* bacterium of claim 1 to the subject.

15. The isolated *Francisella* bacterium of claim 1, wherein the dsbB gene is functionally deleted.

16. The isolated *Francisella* bacterium of claim 1, wherein the pdpB gene is functionally deleted.

17. The isolated *Francisella* bacterium of claim 4, wherein the *Francisella* bacterium is a strain of *Francisella tularensis* subspecies *tularensis*.

18. The method of claim 10, wherein the subject is a human subject.

19. The method of claim 13, wherein the subject is a human subject.

20. The method of claim 14, wherein the subject is a human subject.

* * * * *

UNITED STATES PATENT AND TRADEMARK OFFICE
CERTIFICATE OF CORRECTION

PATENT NO. : 7,972,607 B2  
APPLICATION NO. : 12/280272  
DATED : July 5, 2011  
INVENTOR(S) : Tempel et al.

Page 1 of 2

It is certified that error appears in the above-identified patent and that said Letters Patent is hereby corrected as shown below:

In the Specification:

Column 28, line 36, --the vaccinations because a lower dose (10-1,000-fold fewer bacteria) was used (Tables 3 and 5).-- should be added after "cleared in".

Column 28, lines 37-67 and Column 29, lines 1-39, Table 6 and the first paragraph following Table 6 should be deleted.

Column 31, line 42, the following table and paragraph should be added after "the gene." and before "deletion approx.":

--Table 6-Primers that can be used to amplify genes of *F. tularensis* *

|  | Primer Sequence | SEQ ID NO: |
|---|---|---|
| *dsbB* | | |
| OF | GGGCCCTGGCGCCGTTAGAGATATGTT | 2 |
| IF | CCCATGTGTAAATCAATCACCGGAACAATC | 3 |
| IR | GGTGATTGATTTACACATGGGACATGGTTTCCAA | 4 |
| OR | GTCGACATTTGCATATGTTGCTTGAACA | 5 |
| | | |
| FTT0742 | | |
| OF | CTCGAGATGGTATAGATACACCCCAGCCAG | 6 |
| IF | ATTGCTTTAGTTGGCTGCGGTTATATTCCACACACG GCGAACG | 7 |
| IR | GTTCGCCGTGTGTGGAATATAACCGCAGCCAACTAA AGCAAT AGGTAG | 8 |
| OR | AGATCTACCCTGATCTATCCAACGTGATGG | 9 |
| | | |
| *pdpB* | | |
| OF | CTCGAG AGCACTTTGGACTAAGCACAAACC | 10 |
| IF | CAAAGACCATAAAAAATGCATGTACCTGGGTAATC AAGCACAAAG | 11 |
| IR | TGCTTGATTACCCAGGTACATGCATTTTTTATGGTCT TTGAGGCAG | 12 |
| OR | AGATCTCCAACCATTGTTGCTGTAGAACC | 13 |
| | | |
| *fumA* | | |
| OF | CTCGAG GCTCACCAATTAGTGACCATCCTC | 14 |
| IF | AAAGTTTAGGACCTTGCTGATCACGCTGATATGCTT CATACATTG | 15 |

Signed and Sealed this  
Eleventh Day of December, 2012

David J. Kappos  
*Director of the United States Patent and Trademark Office*

| IR | TATGAAGCATATCAGCGTGATCAGCAAGGTCCTAAACTTTGGAAAC | 16 |
|----|------------------------------------------------|----|
| OR | AGATCTAATTAGCGAGGTTGGCAAGAGGAG | 17 |

* OF = outer forward, IF = inner forward, IR = inner reverse, OR = outer reverse. Upper arm of gene cloned with OF and IR, downstream arm cloned with IF and OR. OF and OR used in the second PCR reaction to connect the two arms and to engineered restriction sites into the OF and OR primers (OF has XhoI and OR has XbaI, except for *dsbB* has ApaI on OF and SalI on OR). In some examples, the engineered restriction sites are not needed, for example if the PCR products are cloned into an intermediate vector (pCR-Blunt-II-TOPO, Invitrogen) and cut out with restriction sites on the vector (such as XhoI and SpeI, except for FTT0742, which uses XhoI and BamHI on the TOPO vector and XhoI and BglII on pDM4 due to SpeI sites in the FTT0742 ORF).

The resulting PCR product is cleaned (for example gel purified using the Qiagen Qiaex kit) and cloned into an intermediate vector, such as pGEM T-Easy (Promega). Once in pGEM, the deletion fragment can be cut out using ApaI and XhoI (whose sites are engineered into the outer primers) and cloned into the pDM4 vector (modified to be kanamycin resistant and chloramphenicol sensitive by adding a full Kan cassette and--